(12) United States Patent
Hong

(10) Patent No.: US 11,033,337 B2
(45) Date of Patent: Jun. 15, 2021

(54) OPTICAL TRACKING SYSTEM AND OPTICAL TRACKING METHOD

(71) Applicant: KOH YOUNG TECHNOLOGY INC., Seoul (KR)

(72) Inventor: Deok Hwa Hong, Gwangmyeong-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 528 days.

(21) Appl. No.: 15/852,573

(22) Filed: Dec. 22, 2017

(65) Prior Publication Data

US 2019/0183583 A1 Jun. 20, 2019

(30) Foreign Application Priority Data

Dec. 20, 2017 (KR) .......................... 10-2017-0176495

(51) Int. Cl.
*A61B 34/20* (2016.01)
*G06T 7/73* (2017.01)
(Continued)

(52) U.S. Cl.
CPC .............. *A61B 34/20* (2016.02); *A61B 5/064* (2013.01); *A61B 6/032* (2013.01); *A61B 34/30* (2016.02);
(Continued)

(58) Field of Classification Search
CPC ......... A61B 34/20; A61B 6/032; A61B 34/30; A61B 5/064; G06T 7/74; G06T 7/00–97;
(Continued)

(56) References Cited

U.S. PATENT DOCUMENTS

| 4,224,829 A * | 9/1980 | Kawabuchi ............ G01N 29/06 73/626 |
| 4,467,187 A * | 8/1984 | Tsunekawa .............. G02B 7/30 250/201.6 |

(Continued)

FOREIGN PATENT DOCUMENTS

| CN | 103460684 | 12/2013 |
| CN | 106415663 | 2/2017 |

(Continued)

OTHER PUBLICATIONS

Mohan ["Bokode: Imperceptible Visual tags for Camera Based Interaction from a Distance" ACM Transactions on Graphics, vol. 28, No. 3, Article 98, Publication date: Aug. 2009], (Year: 2009).*

(Continued)

*Primary Examiner* — Oommen Jacob
(74) *Attorney, Agent, or Firm* — Kile Park Reed & Houtteman PLLC

(57) ABSTRACT

There is provided an optical tracking system for tracking a location and a posture of a marker. The system includes an image capturing device having a first image capturing part, which captures a part of the marker to generate a light field image, and a second image capturing part, which captures an outgoing light emitted from an aperture, and a processor, which determines the posture of the marker based on a first image, which captures a part of a pattern surface and is obtained by extracting an image from the light field image at an infinite focal length, and the location of the marker based on a second image obtained by extracting an image from the light field image at a shorter focal length than the infinite focal length and a third image obtained by capturing the outgoing light emitted from the aperture to the second image capturing part.

15 Claims, 14 Drawing Sheets

(51) Int. Cl.
 *A61B 34/30* (2016.01)
 *A61B 5/06* (2006.01)
 *A61B 6/03* (2006.01)
(52) U.S. Cl.
 CPC ...... *G06T 7/74* (2017.01); *G06T 2207/30204* (2013.01)
(58) Field of Classification Search
 CPC . G06T 2207/30–30248; G06T 7/70–77; G06T 7/97; G06T 7/80; G06T 2207/30204–30208; G06T 1/0007; G06T 7/246; G06T 7/20; G06T 7/73; G06T 2207/10056; H04N 13/02; H04N 5/217; H04N 13/204; G02B 21/365; G02B 21/36
 See application file for complete search history.

(56) References Cited

U.S. PATENT DOCUMENTS

| | | | | |
|---|---|---|---|---|
| 4,818,886 A * | 4/1989 | Drucker | G06K 7/10811 | 250/566 |
| 4,978,860 A * | 12/1990 | Bayley | G06K 7/10722 | 235/462.32 |
| 5,418,357 A * | 5/1995 | Inoue | G06K 7/10881 | 235/462.11 |
| 5,474,548 A * | 12/1995 | Knopp | A61B 3/107 | 351/237 |
| 5,478,997 A * | 12/1995 | Bridgelall | G06K 7/10564 | 235/462.25 |
| 5,770,850 A * | 6/1998 | Bowen | G01J 1/02 | 250/203.1 |
| 7,671,321 B2 * | 3/2010 | Perlman | H04N 5/357 | 250/216 |
| 8,538,064 B2 * | 9/2013 | Rhoads | G06F 16/9554 | 382/100 |
| 8,854,610 B2 * | 10/2014 | Lee | G01B 11/245 | 356/121 |
| 2002/0149691 A1 * | 10/2002 | Pereira | H04N 13/243 | 348/335 |
| 2003/0151679 A1 * | 8/2003 | Amerson | H04N 5/23212 | 348/231.6 |
| 2003/0201328 A1 * | 10/2003 | Jam | G06K 7/10811 | 235/462.22 |
| 2005/0121596 A1 * | 6/2005 | Kam | G01N 21/6458 | 250/201.2 |
| 2009/0129674 A1 * | 5/2009 | Lin | G06T 5/50 | 382/173 |
| 2009/0302116 A1 * | 12/2009 | Tan | G06K 7/10831 | 235/462.35 |
| 2010/0168763 A1 * | 7/2010 | Zhao | A61B 90/94 | 606/130 |
| 2010/0254596 A1 * | 10/2010 | Xiong | G06T 3/4053 | 382/159 |
| 2011/0017826 A1 * | 1/2011 | Mohan | G06K 7/10831 | 235/462.11 |
| 2011/0050893 A1 * | 3/2011 | Lee | H04N 5/247 | 348/137 |
| 2011/0298900 A1 * | 12/2011 | Inaba | H04N 13/239 | 348/47 |
| 2012/0031962 A1 * | 2/2012 | Li | G06K 7/1443 | 235/375 |
| 2013/0027538 A1 * | 1/2013 | Ding | H04N 7/183 | 348/79 |
| 2013/0044190 A1 * | 2/2013 | Hu | G06T 7/55 | 348/50 |
| 2013/0070145 A1 * | 3/2013 | Matsuyama | H04N 5/23212 | 348/333.12 |
| 2013/0259359 A1 * | 10/2013 | Hong | G01N 21/956 | 382/150 |
| 2013/0335521 A1 * | 12/2013 | Lin | H04N 13/239 | 348/36 |
| 2014/0015933 A1 * | 1/2014 | Sato | G02B 21/365 | 348/46 |
| 2014/0327793 A1 * | 11/2014 | Sapir | G02B 7/04 | 348/218.1 |
| 2015/0161802 A1 * | 6/2015 | Christiansen | A61B 90/94 | 348/74 |
| 2015/0264339 A1 * | 9/2015 | Riedel | G06F 3/011 | 348/54 |
| 2016/0287341 A1 | 10/2016 | Hong et al. | | |
| 2017/0193670 A1 | 7/2017 | Lee et al. | | |
| 2017/0200278 A1 * | 7/2017 | Lee | G06T 7/70 | |
| 2018/0046835 A1 | 2/2018 | Hong et al. | | |
| 2019/0183583 A1 * | 6/2019 | Hong | A61B 34/20 | |
| 2019/0239963 A1 | 8/2019 | Hong et al. | | |

FOREIGN PATENT DOCUMENTS

| | | |
|---|---|---|
| JP | 2008-26236 | 2/2008 |
| JP | 2008-216089 | 9/2008 |
| JP | 2016-516526 | 6/2016 |
| JP | 2016-184956 | 10/2016 |
| JP | 2017-522674 | 8/2017 |
| JP | 2017-525937 | 9/2017 |
| JP | 2018-25531 | 2/2018 |
| KR | 10-1406220 | 6/2014 |
| KR | 10-2014-0139698 | 12/2014 |
| KR | 10-2015-0138501 | 12/2015 |
| KR | 10-1627835 | 6/2016 |
| WO | WO-2015183050 A1 * 12/2015 | ............... G06T 7/80 |

OTHER PUBLICATIONS

Korean Office Action with English translation for Korean Application No. 10-2017-0176495, dated Aug. 26, 2019.
You Seong Chae et al., "An Image-Based Coordinate Tracking System Using Afocal Optics for Surgical Navigation"; Progress in Optomechatronic Technologies; Apr. 12, 2014; pp. 141-152.
Ren Ng et al.; "Light Field Photography with a Hand-held Plenoptic Camera"; Stanford Tech Report CTSR Feb. 2005, Feb. 28, 2005; pp. 1-11, Retrieved from the Internet: URL: http://classes.soe.ucsc.edu/cmps290b/Fall05/readings/lfcamera-150dpi.pdf.
Chinese Office Action, with English translation, corresponding to Chinese Application No. or Publication No. 201711403280.0, dated Jan. 28, 2021.

* cited by examiner

FIG. 2
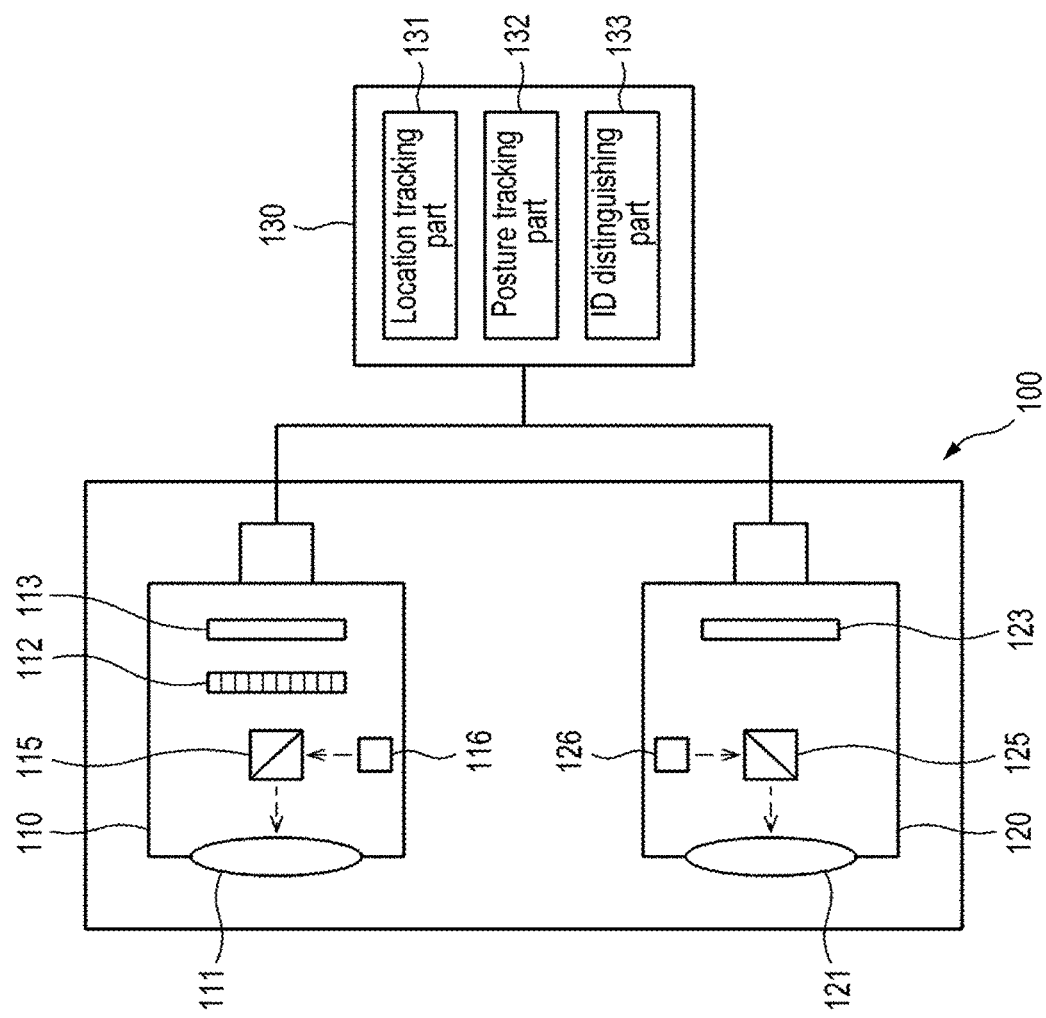
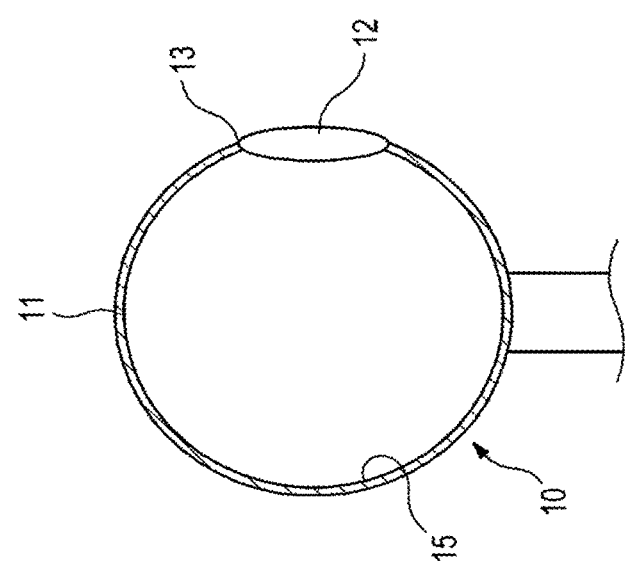

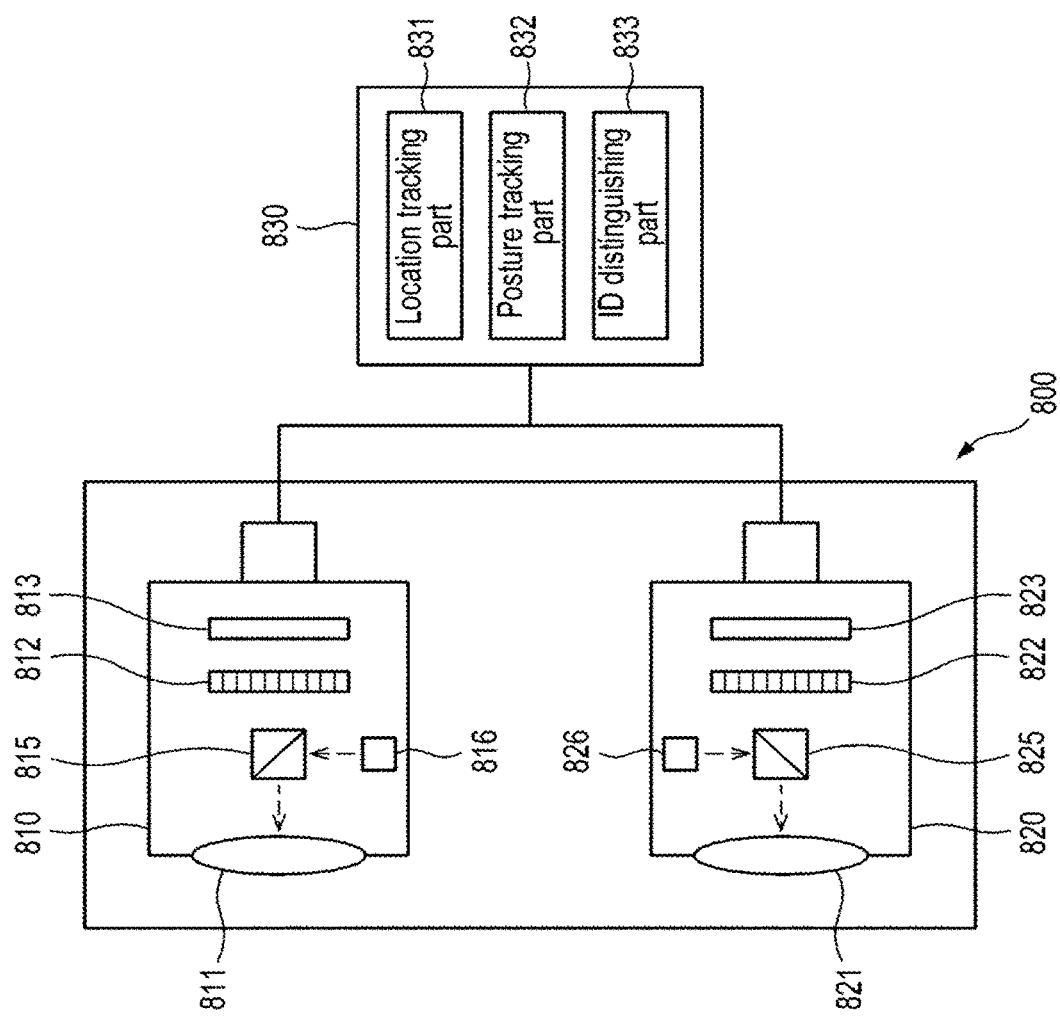
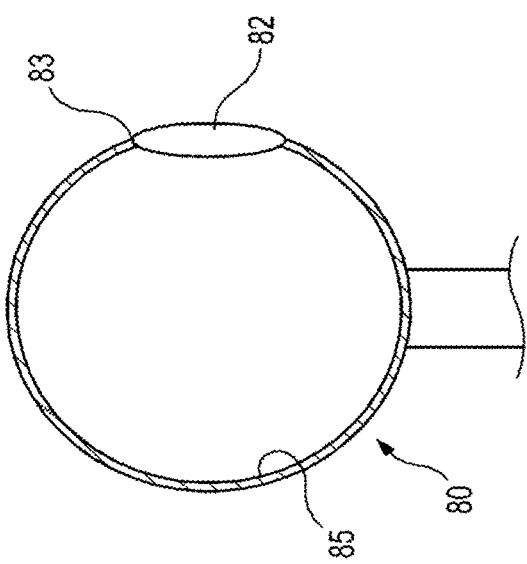

FIG. 14 capturing a first image obtained by extracting an image from a light field image, captured by a first image capturing part, at an infinite focal length, and including a pattern image in which a part of the pattern surface is identifiably captured, a second image obtained by extracting an image from the light field image at a short focal length shorter than the infinite focal length and obtained by capturing an outgoing light emitted through the aperture in a first direction, and a third image obtained by capturing an outgoing light emitted through the aperture in a second direction different from the first direction using a second image capturing part — S1210

Determining a posture of the marker based on the first image — S1220

Determining a location of the marker based on the second image and the third image — S1230

S1200

S1220

S1230

OPTICAL TRACKING SYSTEM AND OPTICAL TRACKING METHOD

CROSS-REFERENCE TO RELATED APPLICATIONS

This application is based upon and claims the benefit of priority from Korean Patent Application No. 10-2017-0176495, filed on Dec. 20, 2017, the entire subject matter of which is incorporated herein by reference.

TECHNICAL FIELD

The present disclosure relates to an optical tracking system and an optical tracking method.

The present disclosure is derived from research conducted as a part of the Robot Industry Fusion Core Technology Development Project of the Ministry of Trade, Industry and Energy. [Project No. 10062800, Project Title: Development of Practical Technology of Medical Imaging based Brain Surgery Robot System through Clinical Trial]

BACKGROUND

An optical tracking system may be used for tracking a target. Recently, in order to perform precise surgery while minimizing a risk of surgical errors, a method has been used that tracks the location (or coordinates) and the posture (or orientation) of a surgical robot or a surgical instrument and utilizes the tracking result for surgery. The location of a target, for example, may be defined as spatial coordinates, such as coordinates on the X-, Y-, and Z-axes of an orthogonal coordinate system. The posture of a target may be defined as a roll, pitch, or yaw. In order to accurately track a target, it is important to accurately recognize the location and the posture of the target, which correspond to six degrees of freedom as described above.

In the optical tracking system, for example, after attaching a reference body, such as a marker, to the target, the marker is tracked in order to determine the location and the posture of the target. The optical tracking system goes through, for example, a process in which a part of the marker is imaged using an image capturing device such as a camera or the like, and the image is read. In this process, a part of the captured image (for example, a boundary portion) may appear blurred or unclear due to various factors. When the marker is tracked based on such an image, there may be generated a difference between the estimated location and posture of the target and the actual location and posture of the target.

SUMMARY

An embodiment of the present disclosure provides an optical tracking system and an optical tracking method capable of accurately measuring the location and posture of a target.

According to one aspect of the present disclosure, there is provided an optical tracking system for tracking a location and a posture of a marker which is attachable to a target and configured so that a pattern surface formed inside the marker is visible through an optical system formed in an aperture, including: an image capturing device including a first image capturing part configured to capture at least a part of the marker to generate a light field image and a second image capturing part configured to capture an outgoing light emitted from the aperture; and a processor configured to determine the posture of the marker based on a first image, which captures a part of the pattern surface and is obtained by extracting an image from the light field image at an infinite focal length, and to determine the location of the marker based on a second image obtained by extracting an image from the light field image at a short focal length shorter than the infinite focal length and a third image obtained by capturing, by the second image capturing part, the first outgoing light emitted from the aperture in a direction different from an emission direction of a second outgoing light directed to the first image capturing part.

In one embodiment, the processor may include: a posture tracking part configured to determine the posture of the marker based on the first image in which the part of the pattern surface visible through the aperture is captured at the infinite focal length; and a location tracking part configured to determine the location of the marker based on the second and third images in which the first and second outgoing lights emitted from the aperture in different directions are respectively captured.

In one embodiment, the first image is obtained by extracting the image from the light field image at the infinite focal length and includes a pattern image in which the part of the pattern surface is identifiably captured, the second image is obtained by extracting the image from the light field image at a focal length of a predetermined range including a location of the target and includes an first outgoing light image in which the second outgoing light directed to the first image capturing part is captured, and the third image includes an second outgoing light image in which the first outgoing light directed to the second image capturing part is captured.

In one embodiment, the posture tracking part may be configured to determine a location of the pattern image from an entire region of the pattern surface and to determine a posture of the target based on the location of the pattern image thus determined.

In one embodiment, the location tracking part may be configured to determine reference coordinates of the first and second outgoing light images captured in the second and third images and to determine the location of the target based on the reference coordinates thus determined and a geometrical relationship between the marker and the first and second image capturing parts.

In one embodiment, the location tracking part may be configured to determine the location of the marker on a three-dimensional space based on a disparity between the reference coordinates of the first and second outgoing light images captured in the second and third images.

In one embodiment, the location tracking part may be configured to construct a stereoscopic image based on the second and third images and to determine the location of the marker on a three-dimensional space.

According to another aspect of the present disclosure, there is provided an optical tracking system for tracking a location and a posture of a marker which is attachable to a target and configured so that a pattern surface formed inside the marker is visible through an optical system formed in an aperture, including: an image capturing device including a first image capturing part and a second image capturing part, each of the first and second image capturing parts configured to capture at least a part of the marker to generate a light field image; and a processor configured to determine the posture of the marker based on a first image, which captures a first part of the pattern surface and is obtained by extracting an image from the light field image, generated by the first image capturing part, at an infinite focal length, and to determine the location of the marker based on a second image obtained by extracting an image from the light field image, generated by the first image capturing part, at a first short focal length shorter than the infinite focal length and a third image obtained by extracting an image from the light field image, generated by the second image capturing part, at a second short focal length shorter than the infinite focal length.

In one embodiment, the first image is obtained by extracting the image from the light field image at the infinite focal length and includes a pattern image in which the first part of the pattern surface is identifiably captured, the second image is obtained by extracting the image from the light field image, generated by the first imagining part, at a focal length of a predetermined range including a location of the target and includes a first outgoing light image in which a first outgoing light directed to the first image capturing part is captured, and the third image is obtained by extracting an image from the light field image, generated by the second image capturing part, at the focal length of the predetermined range and includes a second outgoing light image in which a second outgoing light directed to the second image capturing part is captured.

In one embodiment, the processor may be configured to determine a location of the pattern image from an entire region of the pattern surface and to determine a posture of the target based on the location of the pattern image thus determined, and the processor is configured to determine reference coordinates of the first and second outgoing light images captured in the second and third images, respectively, and to determine the location of the target based on the reference coordinates and a geometrical relationship between the marker and the first and second image capturing parts.

In one embodiment, the second image capturing part is configured to transmit to the processor a fourth image obtained by extracting an image from the light field image, generated by the second image capturing part, at the infinite focal length and including a pattern image in which a second part of the pattern surface is identifiably captured, the processor is configured to determine a location of the pattern image captured in the fourth image from the entire region of the pattern surface and to determine the posture of the target based on the location of the pattern image, and the processor is configured to determine the posture of the target based on an average value of the posture of the target determined from the first image and the posture of the target determined from the fourth image.

In one embodiment, the processor may be configured to determine a location and a posture of the target from a pattern image captured in the first image.

According to a further aspect of the present disclosure, there is provided an optical tracking method for tracking a location and a posture of a marker which is attachable to a target and configured so that a pattern surface formed inside the marker is visible through an optical system formed in an aperture, including: capturing a first image obtained by extracting an image from a light field image, captured by a first image capturing part, at an infinite focal length, and including a pattern image in which a part of the pattern surface is identifiably captured, a second image obtained by extracting an image from the light field image at a short focal length shorter than the infinite focal length and obtained by capturing an outgoing light emitted through the aperture in a first direction, and a third image obtained by capturing an outgoing light emitted through the aperture in a second direction different from the first direction using a second image capturing part; determining the posture of the marker based on the first image; and determining the location of the marker based on the second image and the third image.

In one embodiment, the determining the posture of the marker may include: determining a location of the pattern image included in the first image from an entire region of the pattern surface; and determining a posture of the target based on the location of the pattern image thus determined.

In one embodiment, the determining the location of the marker may include: determining reference coordinates of the outgoing light images captured in the second and third images; and determining a location of the target based on the reference coordinates thus determined and a geometrical relationship between the first and second directions in which the outgoing lights are directed.

According to the embodiments of the present disclosure, it is possible to simultaneously acquire an image in which a pattern image is identifiably captured and an image in which the position of an aperture region is identifiably captured, from a light field image.

In addition, it is possible to improve the accuracy of a reference position of an outgoing light image in a captured image and to improve the precision of the optical tracking system.

BRIEF DESCRIPTION OF THE DRAWINGS

Embodiments of the inventive aspects of this disclosure will be understood with reference to the following detailed description, when read in conjunction with the accompanying drawings.

FIG. 2 is a block diagram of an optical tracking system according to an embodiment of the present disclosure.

FIG. 11 is a block diagram of an optical tracking system according to another embodiment of the present disclosure.

FIG. 14 is a flowchart showing an optical tracking method according to a further embodiment of the present disclosure.

DETAILED DESCRIPTION

Figure 1:
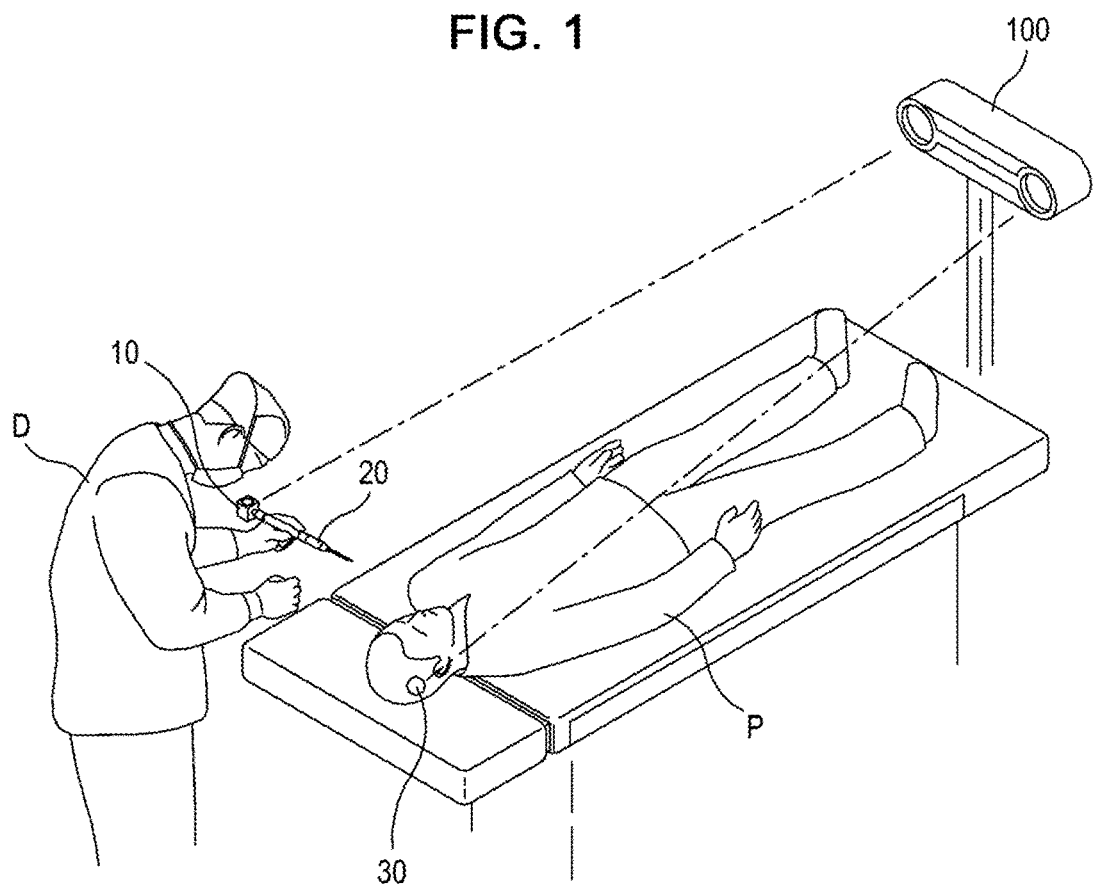
FIG. 1 is a view showing an example in which an optical tracking system is used for surgery according to an embodiment of the present disclosure.

Embodiments of the present disclosure are only examples that are illustrated for the purpose of explaining the present disclosure. The embodiments of the present disclosure may be conducted in various manners, and the present disclosure shall not be construed to be limited to the embodiments described below or to the detailed description of the embodiments.

The term "part" used in the present disclosure refers to a software element or a hardware element, such as FPGA (field-programmable gate array), ASIC (application specific integrated circuit), etc. However, the "part" is not limited to hardware and software. The "part" may be configured to be in a storage medium that can be addressed, and may be configured to reproduce one or more processors. Accordingly, as an example, the "part" includes elements, such as software elements, object-oriented software elements, class elements, task elements, etc., processors, functions, attributes, procedures, subroutines, program code segments, drivers, firmware, micro-codes, circuits, data, databases, data structures, tables, arrays, and variables. Functions that are provided in the elements and "part" may be combined into fewer elements and "parts," or may be further divided into additional elements and "parts."

All the technical terms and scientific terms in the present disclosure include meanings or definitions that are commonly understood by those of ordinary skill in the art unless otherwise defined. All terms in the present disclosure are selected for the purpose of describing the present disclosure more clearly, and are not selected to limit the scope of the present disclosure.

The singular expressions that are described in the present disclosure may encompass plural expressions unless otherwise stated, which will be also applied to the singular expressions recited in the claims.

The expressions, such as "first," "second," etc., which are shown in various embodiments of the present disclosure, are used to separate a plurality of elements from each other, and are not intended to limit an order or importance of the corresponding elements.

The expressions, such as "include" or "have," which are used in the present disclosure, should be appreciated as open-ended terms that include a possibility of including other embodiments unless particularly otherwise stated in the phrase or sentence that contains the corresponding expressions.

In the present disclosure, the expression "based on" will be used to describe one or more factors that affect an act or operation of a decision or determination that is described in the phrase that contains the corresponding expression, and does not exclude additional factors that affect the act or operation of the decision or determination.

In the present disclosure, the description that one element is "connected," or "coupled" to another element should be appreciated to indicate that one element may be directly connected, or coupled, to another element, and should be further understood that a new element may be interposed between one element and another element.

Hereinafter, the embodiments of the present disclosure will be described in detail with reference to the accompanying drawings. The same reference numeral will be used for the same element throughout the drawings, and a duplicate description of the same element will be omitted.

<Optical Tracking System>

FIG. 1 is a view showing an example in which an optical tracking system 1 according to an embodiment of the present disclosure is used for surgery.

As shown, a doctor D may proceed with surgery for a patient P by using a surgical instrument 20 and the optical tracking system 1 which includes an image capturing device 100. A marker 10 may be attached to the surgical instrument 20 that is used by the doctor D, and another marker 30 may be attached to a target, such as an affected portion of the patient P. The image capturing device 100 of the optical tracking system 1 may capture and obtain a pattern image for the whole pattern or a part of a pattern formed on the marker 10 and/or 30. The pattern image may be captured in a partial region in a frame of a captured image that is outputted by an image sensor included in an image capturing part of the image capturing device 100.

When the pattern image is obtained, one or more sub-patterns may be extracted from the pattern image as a basic unit constituting the pattern of the marker. According to some embodiments, locations of the one or more extracted sub-patterns in the entire pattern may be determined, and the posture of the marker 10 and/or 30 may be determined based on the determined locations of the sub-patterns in the entire pattern. In this case, the posture of the marker 10 and/or 30 may be referred to a relative three-dimensional direction or orientation of the marker 10 and/or 30 with respect to the image capturing device 100.

According to one embodiment, the image capturing device 100 may include two or more image capturing parts which may be, for example, cameras capable of capturing an image for at least a part of the marker. Specifically, each of the image capturing parts may capture an image from, for example, the light that goes from an aperture of the marker 10 and/or 30 to each of the image capturing parts. The location of one marker 10 and/or 30 may be determined using triangulation based on two images having a stereoscopic relationship among the images captured by two or more cameras.

When the location and the posture of the marker 10 and/or 30 are obtained as described above, the location and the posture of a target to which the marker 10 and/or 30 is attached may be determined based on a geometrical relationship between the marker 10 and/or 30 and the target to which the marker 10 and/or 30 is attached.

As will be described in detail below, according to the optical tracking system 1 according to an embodiment of the present disclosure, the location and the posture of the target corresponding to six degrees of freedom may be determined by using at least one marker.

According to the optical tracking system 1 of the present disclosure, even when one marker 10 is attached to the surgical instrument 20 as a target, the location and the posture of the target may be tracked based on a pattern formed on the marker 10. Therefore, a light or small marker 10 may be attached to the surgical instrument 20, and the doctor D may proceed with surgery by using the surgical instrument 20 having the marker attached thereto without concerning about a size or weight of the marker 10.

Although the marker and the optical tracking system 1 according to the present disclosure are used in the surgery of a patient by a doctor in the embodiments described above, they may also be used in various other instances for determining the location and the posture of a target by using a marker. For example, the marker and the optical tracking system, according to the present disclosure, may be used for determining the location and the posture of a surgical instrument that is attached to a surgical robot when a patient undergoes surgery using the surgical robot. In another example, the marker and the optical tracking system, according to the present disclosure, may be used for determining the location and the posture of a specific instrument and/or target when a specific operation is performed with respect to the target using the instrument by an operator or surgical robot. Various embodiments of the marker and the optical tracking system of the present disclosure, which have been described through the examples of FIGS. 1 and 2, will be described in more detail below.

FIG. 2 depicts a block diagram of the optical tracking system 1 according to an embodiment of the present disclosure.

The optical tracking system 1 may include a marker 10, an image capturing device 100, and a processor 130. The marker 10 may include a pattern surface 15 on which a pattern is formed, and an optical system 12, such as lenses or the like, which is configured to allow at least a part of the pattern, which uniquely appears depending on a viewing direction from the outside of the marker, to be identified (or visually recognized) from the outside of the marker 10. According to one embodiment, the marker 10 may be attached to a target whose location and posture are measured by the optical tracking system 1, or may be implemented as the entirety or a part of the target. By measuring the location and the posture of the marker 10, the location and the posture of the target to which the marker 10 is attached may be measured.

The contour of the marker 10 may have a shape that facilitates installation of the pattern surface 15 and the optical system 12 such as a lens or the like. In one embodiment, the contour 11 of the marker 10 may have a curved shape. When the marker 10 has a curved shape in this way, the pattern surface 15 on which a pattern is formed may be embodied on at least a part of the inner or outer surface having a spherical shape, and the optical system 12 may be embodied in an aperture 13 opposite to the pattern surface 15 on the inner surface having a spherical shape. In another embodiment, the contour 11 of the marker 10 may have, for example, a hexahedral or cylindrical shape. When the contour 11 has a cylindrical shape, the optical system 12 may be provided in the aperture 13 formed on one side surface of the cylindrical shape, and the pattern surface 15 may be provided on the other side surface opposite to one side surface. In this configuration, the pattern formed on the pattern surface 15 may be visually recognized from the outside through the body of the cylinder and the optical system 12.

In one embodiment, the image capturing device 100 may capture a plurality of images including at least a part of the marker 10. The processor 130 may receive the plurality of images from the image capturing device 100 and may track the location and the posture of the marker 10 based on the plurality of images. The image capturing device 100 may include first and second image capturing parts 110 and 120, each of which is configured to capture a different image. The first and second image capturing parts 110 and 120 may capture images formed by the outgoing lights reflected from the marker 10 and emitted in different directions.

The first image capturing part 110 may include a lens 111, a lens array 112, and an image sensor 113. That is, the first image capturing part 110 may have a structure of a light field camera configured to capture a light field image. Accordingly, the first image capturing part 110 may generate a light field image by capturing an image formed by the outgoing light reflected from the pattern surface 15 and entering the lens 111. In addition, the second image capturing part 120 may include a lens 121 and an image sensor 123. Accordingly, the second image capturing part 120 may obtain another image formed by the outgoing light coming into the lens 121 in a direction different from the light directed to the first image capturing part 110 after being reflected from the pattern surface 15 of the marker 10.

In one embodiment, each of the first and second image capturing parts 110 and 120 may include at least one light source 116 or 126 that irradiates light toward the marker 10 or the pattern in order to enhance the light incident on the image capturing device 100 through the optical system 12 so that the pattern can clearly be identified outside the marker 10. In this case, the marker 10 may operate as a passive marker. Each of the first and second image capturing parts 110 and 120 may include a beam splitter 115 or 125 that irradiates the light generated from the light source 116 or 126 toward the marker 10 through the lens 111 or 121.

In FIG. 2, the light sources 116 and 126 are disposed inside the first and second image capturing parts 110 and 120. However, the present disclosure is not limited thereto. The light sources 116 and 126 may be disposed outside the image capturing device 100. According to another embodiment, the light sources may be installed inside the marker 10 so as to irradiate the light toward the front or back surface of the pattern surface 15. In this case, the marker 10 may operate as an active marker.

In one embodiment, when the optical tracking system 1 is operating within a surgical system such as a surgical navigation system or the like, the marker 10 may be attached to at least one target including a surgical tool, a portion of a surgical robot or an affected portion of a patient. When a plurality of markers is used, the locations and the postures of the markers may be tracked sequentially or simultaneously. In this case, in order to track the locations and the postures of the plurality of markers, the processor 130 may distinguish the markers attached to the respective targets through the identifications (IDs) of the markers.

According to a further embodiment, the optical tracking system 1 may track the locations and the postures of two markers having a predetermined geometrical relationship. For example, the optical tracking system 1 may simultaneously track the locations and postures of the marker 10 attached to the surgical instrument 20 shown in FIG. 1 and the marker 30 attached to the head of a patient. The optical tracking system may obtain pattern images of patterns formed on two markers, respectively, through the image capturing device. The locations of two markers may be determined based on the predetermined geometrical relationship and the relationship between the location of at least a part of the pattern on the pattern image and the location of at least the corresponding part of the pattern on each of the markers. The postures of the markers may be determined in the same manner as described above.

In one embodiment, the processor 130 may include a posture tracking part 132 for determining the posture of the marker 10 based on a first image obtained by capturing a part of the pattern surface 15 viewed through the aperture 13 at an infinite focal length, a location tracking part 131 for determining the location of the marker 10 based on second and third images respectively obtained by capturing the outgoing lights emitted through the aperture 13 in different directions at a focal length shorter than the infinite focal length, and an ID distinguishing part 133 for distinguishing the markers attached to the respective targets through the IDs of the markers to track the locations and the postures of the markers. The ID distinguishing part 133 may distinguish the ID of the marker 10 from the pattern image included in the first image.

The infinite focal length may mean, for example, a length corresponding to a position considerably farthest away from the marker 10 with respect to the image capturing device 100. Further, the focal length shorter than the infinite focal length (hereinafter referred to as "shorter focal length") may be a predetermined range of focal lengths within which the location of the target is included. That is, since the marker 10 is attached to the target, the shorter focal length may be a predetermined range of focal lengths within which the location of the marker 10 is included.

Figure 3:
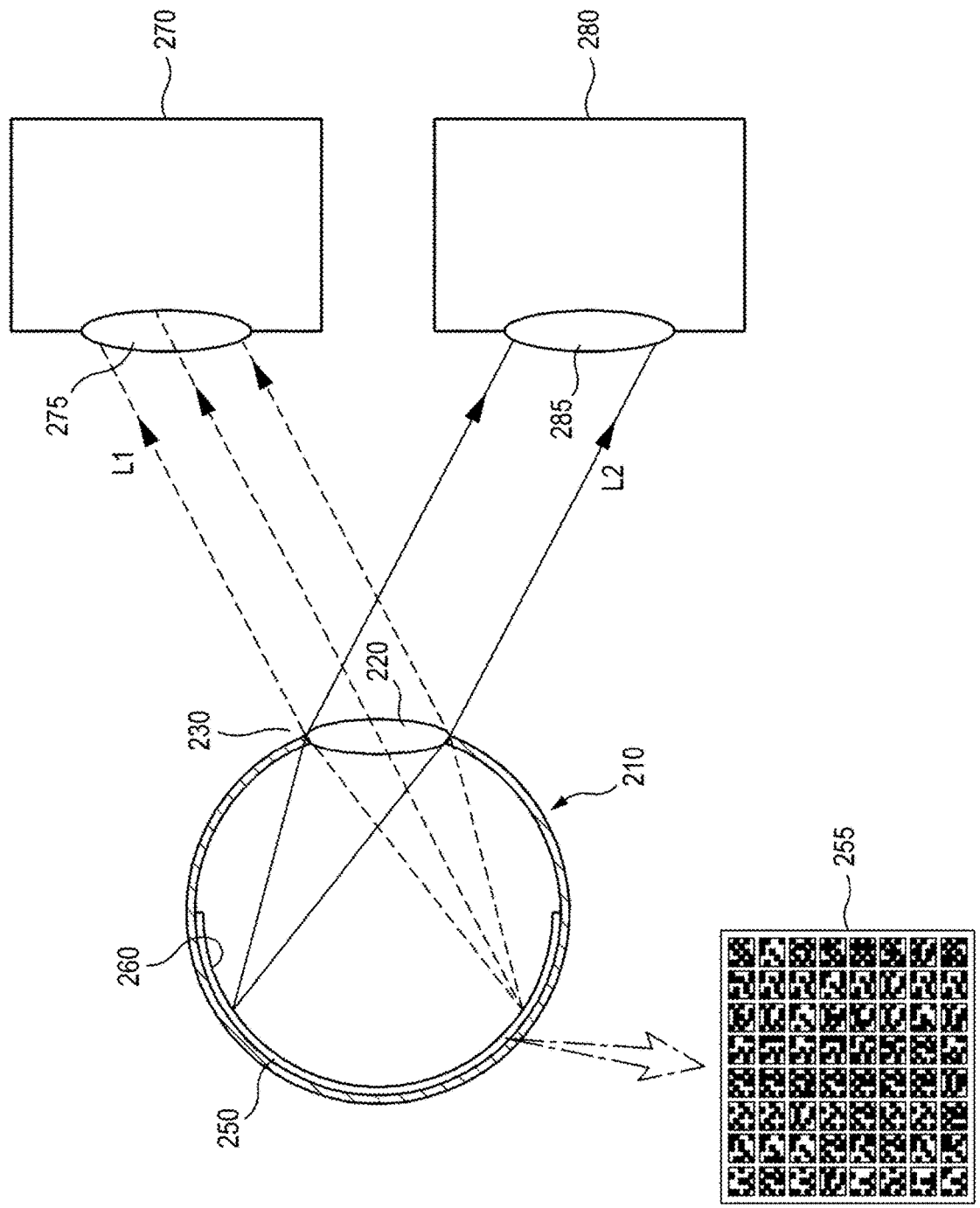
FIG. 3 is a view showing an example in which the outgoing lights emitted from an aperture of a marker in different directions are captured by image capturing parts in accordance with an embodiment of the present disclosure.

FIG. 3 is a view illustrating an example in which the outgoing lights L1 and L2 emitted from the aperture 230 of the marker 210 in different directions are captured by the image capturing parts 270 and 280 according to an embodiment of the present disclosure.

Referring to FIG. 2, the first image capturing part 270 may have a structure of a light field camera. The second image capturing part 280 may have a structure of a camera for capturing an image at a shorter focal length. Furthermore, the first image capturing part 270 may capture a pattern image by imaging a part of the pattern surface 250 at an infinite focal length, and the second image capturing part 280 may capture the outgoing light reflected from the pattern surface 250 of the marker 210 and entering the optical system 220 at a shorter focal length.

The marker 210 may be positioned within the field of view (FOV) of each of the first and second image capturing parts 270 and 280. The optical system 220 formed in the aperture 230 may be disposed to face the first and second image capturing parts 270 and 280. In this regard, the light reflected from the pattern surface 250 may be emitted as parallel outgoing light L1 through the optical system 220 and may reach the lens 275 of the first image capturing part 270 where the light may be captured as a pattern image. The outgoing light L2 emitted from the optical system 220 of the marker 210 in a direction different from the outgoing light L1 directed toward the first image capturing part 270 may reach the lens 285 of the second image capturing part 280 and may be captured as an outgoing light image.

In one embodiment, the first image capturing part 270 may form an infinite optical system together with the marker 210. The pattern surface 250 on which a pattern 255 is formed may be disposed inside the marker 210 such that a pattern image is transferred to the first image capturing part 270 through the optical system 220 in the form of the outgoing light L1. The depth of field of the image sensor included in the first image capturing part 270 may be set so as to encompass a region from the point farther than the location of the marker 210 to the infinite point where the pattern image is formed by the optical system 220 of the marker 210. In this case, the image sensor included in the first image capturing part 270 may capture a pattern image on a part of the pattern formed in the marker 210, regardless of whether the distance from the marker 210 is changed in response to the movement of the marker 210. In addition, the first image capturing part 270 may capture the pattern image without adjusting the depth of field or the magnification even when the marker moves away from or comes close to the first image capturing part 270. Therefore, if the infinite optical system is configured as described above, at least a part of the pattern may be identified from the pattern image captured by the first image capturing part 270, regardless of how far the marker 210 is located away from the image capturing device. In another embodiment, when the pattern surface 250 is disposed inside the marker 210, the optical system 220 of the marker 210 may constitute an infinite optical system together with lenses 275 and 285 of the first and second image capturing parts 270 and 280.

In one embodiment, the pattern 255 is formed such that the location of each of the sub-patterns is uniquely determined throughout the entire pattern. Therefore, the information on the location of each sub-pattern in the entire pattern may be extracted from the pattern image of the pattern. Specifically, the pattern 255 may include aperiodic sequences that are repeatedly arranged. For example, each aperiodic sequence may be a Pseudo-Random Binary Sequence (PRBS), and more specifically, may be a De Bruijn Sequence. In this case, the "aperiodic sequence," as described above, may mean that it has a maximized auto-correlativity or a plurality of sub-sequences included in the corresponding sequence is not arranged in a periodic manner. In addition, the pattern 255 may be formed so as to provide the ID of the marker.

Figure 4:
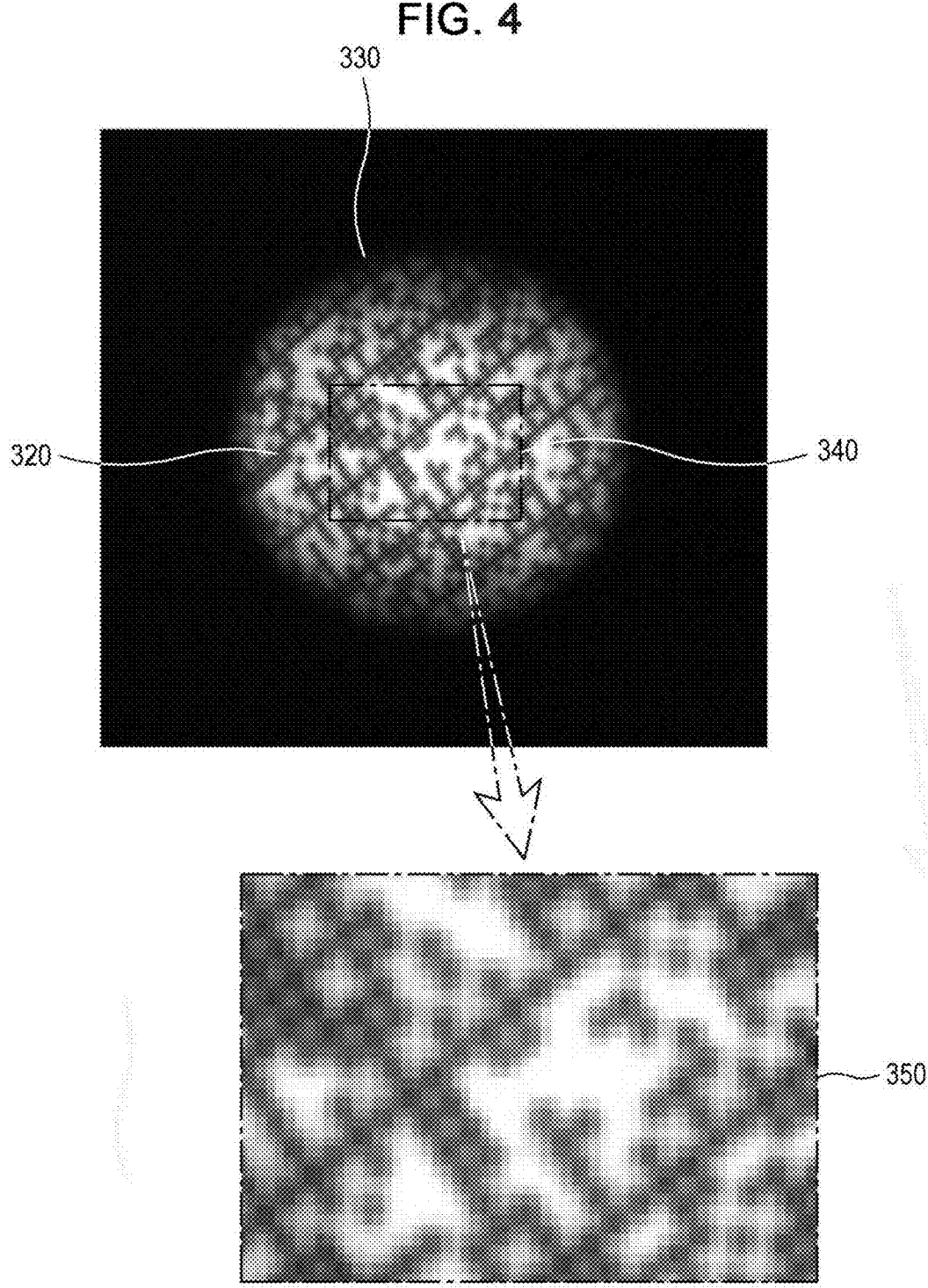
FIG. 4 is a view for illustrating an image captured in an image capturing part in accordance with an embodiment of the present disclosure.

FIG. 4 is a view for illustrating an image captured in the image capturing part in accordance with an embodiment of the present disclosure.

In one embodiment, the image capturing part may capture an image of at least a part of the pattern formed on the marker to determine the location and the posture of a target (for example, a surgical instrument) to which the marker is attached. There may be a predetermined geometrical relationship between the marker and the target. When the posture of the marker is tracked, the posture of the target may be tracked using the predetermined geometrical relationship with the target.

The image capturing part constituting the infinite optical system together with the marker may acquire a corrected image by subjecting a captured image 300 actually captured by the image sensor to predetermined image processing. The captured image 300 is such that the periphery around the pattern portion is not completely dark and the objects located at the field of view of the image capturing device are blurred. The image processing may be, for example, an operation by which the difference between bright and dark portions in the captured image is enhanced.

In one embodiment, the captured image 300 may include a pattern image 320 formed at a predetermined location. An imaginary boundary portion 330 surrounding the pattern image 320 may correspond to the location of the aperture of the marker and may distinguish the pattern image 320 from the peripheral portion 310. A sub-pattern 350 included in the pattern image 320 may be read through a pattern window 340 in a posture determination part of the processor. After the original image (not shown) is subjected to the image processing, the pattern image 320 becomes prominent just like the captured image 300 shown in FIG. 4. The peripheral portion 310 becomes dark, and the boundary portion 330 is blurred.

The peripheral portion 310 of the captured image 300 excluding the pattern image 320 is a portion that is relatively darker than the pattern surface of the marker corresponding to the pattern image 320 and may be captured in a imageless state (for example, a black-out state). That is, the area having no depth of field and the area having a relatively small light amount are darkened by the image sensor of the image capturing device. The darkened areas may become the peripheral portion 310. In addition, the image sensor of the image capturing part constituting the infinite optical system together with the optical system of the marker has a focal length set to a long distance or an infinite distance, whereby all the objects existing in a short distance falling within a marker operation range may be severely blurred. Moreover, the pattern image 320 may be strongly prominent within the captured image 300 because the outgoing light emitted from the aperture of the marker is relatively bright compared with the ambient light. If the light used for capturing the image of the marker is controlled through illumination and filtering, the difference in brightness between the pattern image 320 and the peripheral portion 310 may be larger in the captured image 300.

In one embodiment, when the image capturing part of the optical tracking system captures the pattern image 320 using the outgoing light reflected from the pattern surface formed on the marker, the posture determination part of the processor may determine the posture of the marker based on the location in the entire pattern of each sub-pattern 350 included in the pattern image 320. For example, a part of the pattern 255 shown in FIG. 3 may be included in the captured pattern image 320. The processor may receive the captured image 300 from the image capturing part, may conduct the image processing, and then may identify the sub-pattern 350 through a pattern window 340 in the pattern image 320. The size of the pattern window 340 may be equal to or greater than the size of the sub-pattern 350. That is, the posture tracking part of the processor may determine the location of the corresponding sub-pattern in the entire pattern and may determine the posture of the marker based on the location of the sub-pattern thus determined.

Figure 5:
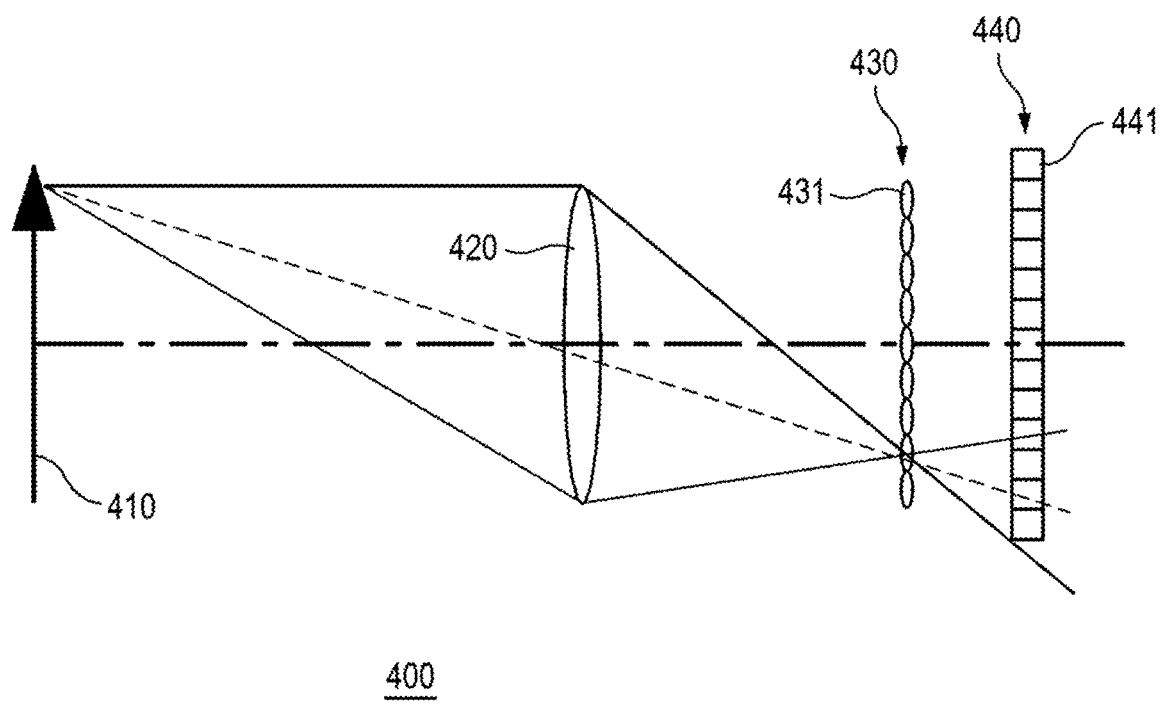
FIG. 5 is a view for illustrating an image capturing part having a structure of a light field camera.

FIG. 5 is a view for illustrating an image capturing part 400 having a structure of a light field camera.

In one embodiment, the image capturing part 400 may include a lens 420, a lens array 430 and an image sensor 440 sequentially disposed from a subject 410. The subject 410 may be an aperture of a marker or a part of a pattern formed on the marker. The image capturing part 400 shown in FIG. 5 is an example of an arrangement structure for obtaining a light field image. A structure different from the structure shown in FIG. 5 may be used to obtain a light field image.

In one embodiment, the lens 420 may condense the light coming from the subject 410. The lens 420 may be a convex lens having one focal length so that the light coming from the subject 410 is condensed at one point. When the lens 420 is implemented using a plurality of lenses or the like, a plurality of lenses may be defined as a single thin lens according to a well-known thin lens theory. Accordingly, the diameter, the focal length and the center of the lens 420 may be represented by the diameter, the focal length and the center of one thin lens thus defined.

In one embodiment, the lens array 430 may disperse the light coming through the lens 420 and may condense the light at a plurality of points formed at different locations. The lens array 430 may be composed of a plurality of sub-lenses 431. In one embodiment, the lens array 430 may be disposed closer to the lens 420 than the focal length of the lens 420. In another embodiment, the lens array 430 may be disposed farther from the lens 420 than the focal length of the lens 420.

In one embodiment, the lens array 430 may be disposed at a position corresponding to the focal length of the lens 420. In this case, the focal point of the light coming from the lens 420 may be formed on one of the sub-lenses 431. In addition, an image sensor 440 may be fixedly installed at a position corresponding to the focal length of each of the sub-lenses 431 included in the lens array 430.

In one embodiment, the image sensor 440 may sense the light that has passed through the lens array 430. In addition, the image sensor 440 may obtain a light field image that includes a plurality of unit images corresponding to a plurality of points. The image sensor 440 may include at least one image capturing element of an arbitrary type configured to acquire a captured image of an arbitrary object and may include, for example, a Charge Coupled Device (CCD) sensor or a Complementary Metal-Oxide Semiconductor (CMOS) sensor. The image sensor 440 may include a plurality of pixels 441.

In one embodiment, the image sensor 440 may output a light field image having, for example, a format of a photo aggregate file, at one shot. The photo aggregate file may include a plurality of unit images having focuses of a subject at positions corresponding to the focuses of a plurality of sub-lenses and having different depths of field. In each unit image, the color information and the direction information of the light may be stored together according to X and Y coordinates.

In one embodiment, the respective unit images have different depths of field but can be obtained from the same target. The appearances of the target shown in the respective unit images may be substantially the same. The positions of a clearly visible region and a blurred region may differ from each other. The clearly visible region may be a region focused by the corresponding sub-lens 431 and having a depth of field. The blurred region may be a region other than the clearly visible region.

The light field camera may be configured to post-determine a depth of field after capturing an image of a subject and to combine images having different depths of field. Thus, the image sensor of the light field camera may have post-determined variable depths of field. The light field image generated by the light field camera may include a plurality of unit images for storing the color information and the direction information of the light together.

In one embodiment, the light field camera implemented by the image capturing part 400 may transmit to the processor a first image, which is obtained by synthesizing images with depths of field ranging from a long distance to an infinite distance, so as to clearly capture an image of a subject 410, i.e., a part of a pattern surface of a marker located at an infinite position.

In another embodiment, the first image capturing part 400 may perform a refocusing process using a plurality of unit images. In the refocusing process, an image having a desired depth may be newly extracted by combining the desired depth of field among the pixels of the light field image and the color information of the pixels corresponding to the inversely calculated light path or direction. This makes it possible to generate a first image from which a pattern image is clearly identified.

Figure 6:
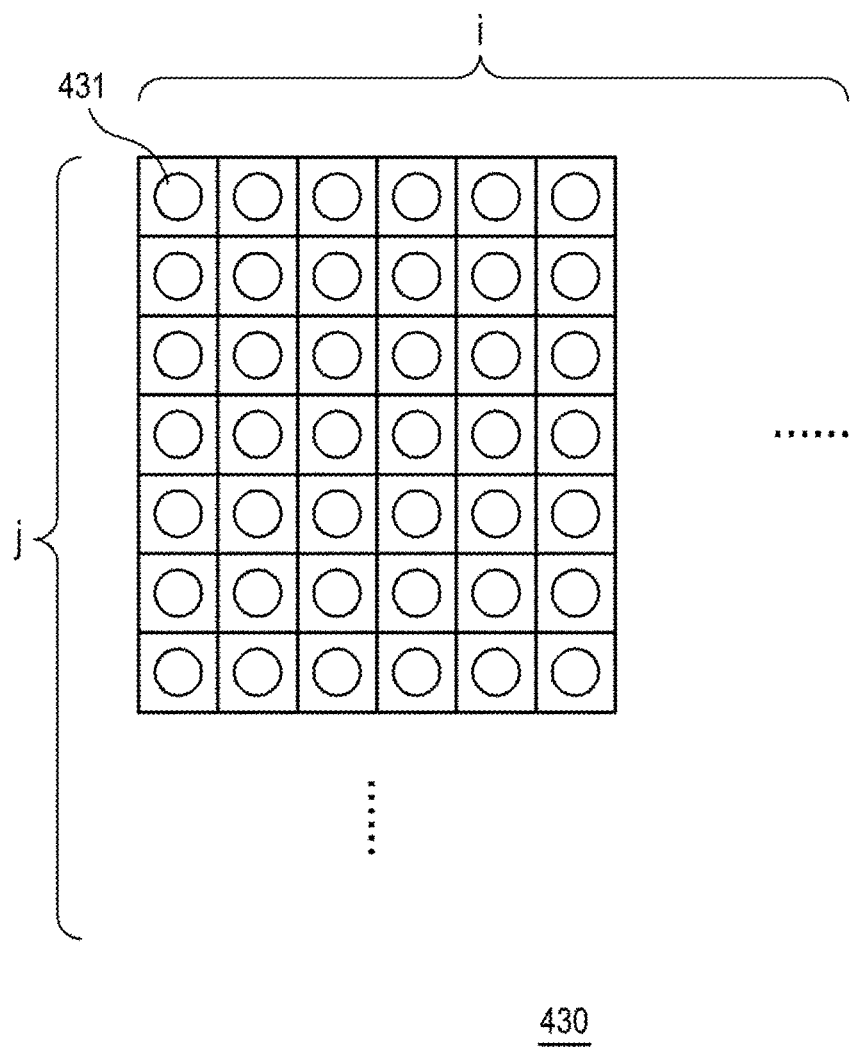
FIG. 6 is a view for illustrating the lens array shown in FIG. 5.

FIG. 6 is a view for illustrating the lens array 430 shown in FIG. 5.

In one embodiment, the plurality of sub-lenses 431 included in the lens array 430 may be provided as N micro lenses (where N>1 and N is a natural number). That is, N may mean a plurality of pieces. For example, in the lens array 430, i sub-lenses 431 may be arranged for each row, and j sub-lenses may be arranged for each column. Thus, the N micro lenses may be composed of i×j matrices. As an example, in order to form a more compact light field, the lens array 430 may have a configuration in which about 1000×1000 micro lenses are arranged. The arrangement and the number of the micro lenses may vary depending on various conditions such as the physical properties of the lenses and the micro lenses, the imaging environment, the required resolution of the unit images, the number of pixels of the image sensor or the like.

In one embodiment, the N micro lenses corresponding to the sub-lenses 431 may disperse the light coming through the lenses toward N points. In one embodiment, the image sensor shown in FIG. 5 may be divided into N regions corresponding to the N points formed by the N micro lenses. That is, the focuses of the N micro lenses may be formed so as to be dispersed into the N regions of the image sensor.

In one embodiment, when capturing N unit images in the N regions, the light field image may include N unit images having different depths of field. Further, the processor may select an image in which a depth of field is formed at a predetermined position, from among the N images. The processor may select at least one image having an infinite focal length or a short focal length from among the N images. For example, the image capturing part may extract an image having an infinite focal length from a light field image in order to capture an image in which the pattern surface of the marker is formed, and may extract an image having a short focal length in order to capture an outgoing light image.

Figure 7:
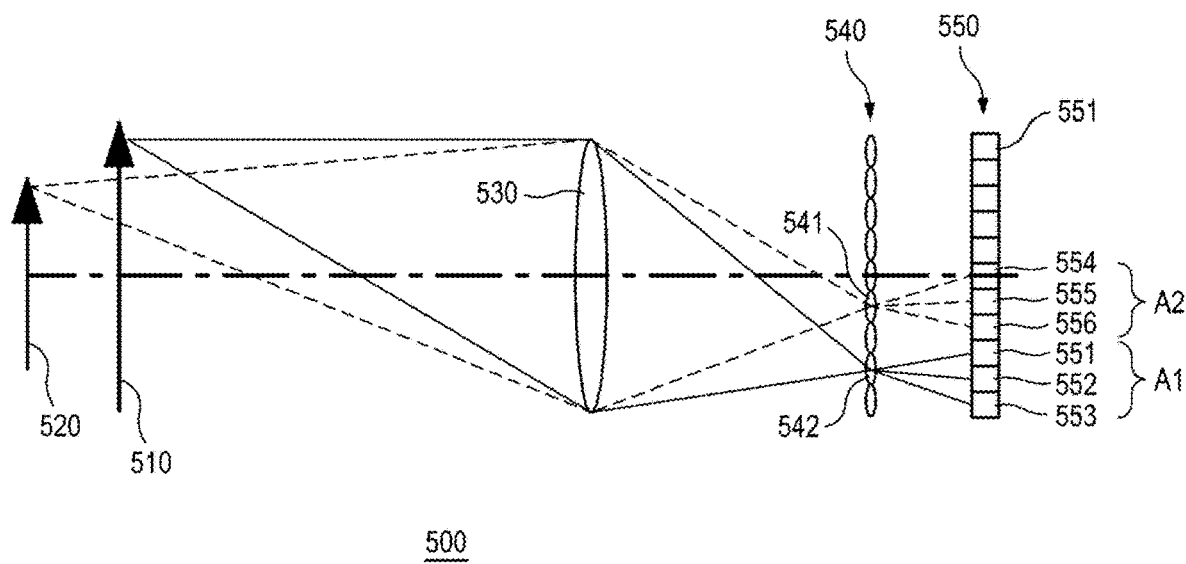
FIG. 7 is a view illustrating a process in which the depths of field of a plurality of unit images included in a light field image acquired by an image capturing part are formed differently.

FIG. 7 is a view illustrating a process in which the depths of field of a plurality of unit images included in the light field image obtained by an image capturing part are formed differently.

The image capturing part 500 may include a lens 530, a lens array 540 and an image sensor 550. A first subject 510 may be disposed closer to the lens 530 than a second subject 520. In one embodiment, the first subject 510 may correspond to the aperture 230 of the marker shown in FIG. 3, and the second subject 520 may correspond to the pattern surface 250 shown in FIG. 3.

The light coming from the upper end of the first subject 510 may be condensed through the lens 530 and may focus on the sub-lens 542 disposed on the lower side of the lens array 540. The light coming from the sub-lens 542 may reach a region A1 disposed on the lower side of the image sensor 550. Accordingly, the amount of the light coming from the upper end of the first subject 510 may be distributed mainly in the lower region A1, and a smaller amount of light may be distributed in the remaining region. That is, the appearance of the upper end of the first subject 510 may be clearly captured in the pixels 551, 552 and 553 included in the lower region A1.

The light coming from the upper end of the second subject 520 may be condensed through the lens 530 and may be focused on the sub-lens 541 existing in the intermediate portion of the lens array 540. The light coming from the sub-lens 541 may reach a region A2 disposed in the intermediate portion of the image sensor 550. Accordingly, the amount of the light coming from the upper end of the second subject 520 may be distributed mainly in the intermediate region A2, and a smaller amount of light may be distributed in the remaining region. That is, the appearance of the upper end of the second subject 520 may be clearly captured in the pixels 554, 555 and 556 included in the intermediate region A2.

Since the amount of the light coming from the second subject 520 is small in the lower region A1, the appearance of the second subject 520 may be captured in a blurred state. In addition, since the amount of the light coming from the first subject 510 is small in the intermediate region A2, the appearance of the first subject 510 may be captured in a blurred state. Thus, the lower region A1 may output a unit image having a depth of field with respect to the first subject 510, and the intermediate region A2 may output a unit image having a depth of field with respect to the second subject 520.

According to the above description, when a subject is imaged through the image capturing part according to one embodiment, a light field image including a plurality of unit images having different depths of field may be obtained.

Figure 8:
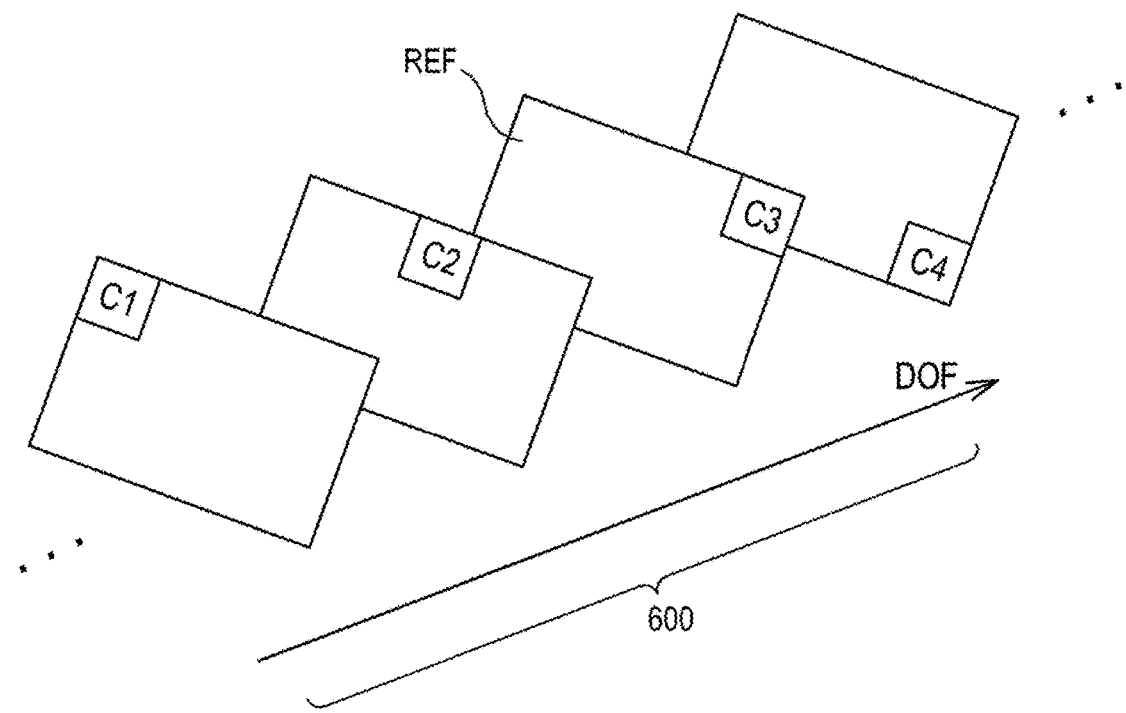
FIG. 8 is a view for illustrating a light field image including a plurality of unit images having different depths of field.

FIG. 8 is a view for illustrating a light field image 600 including a plurality of unit images having different depths of field.

Figure 9:
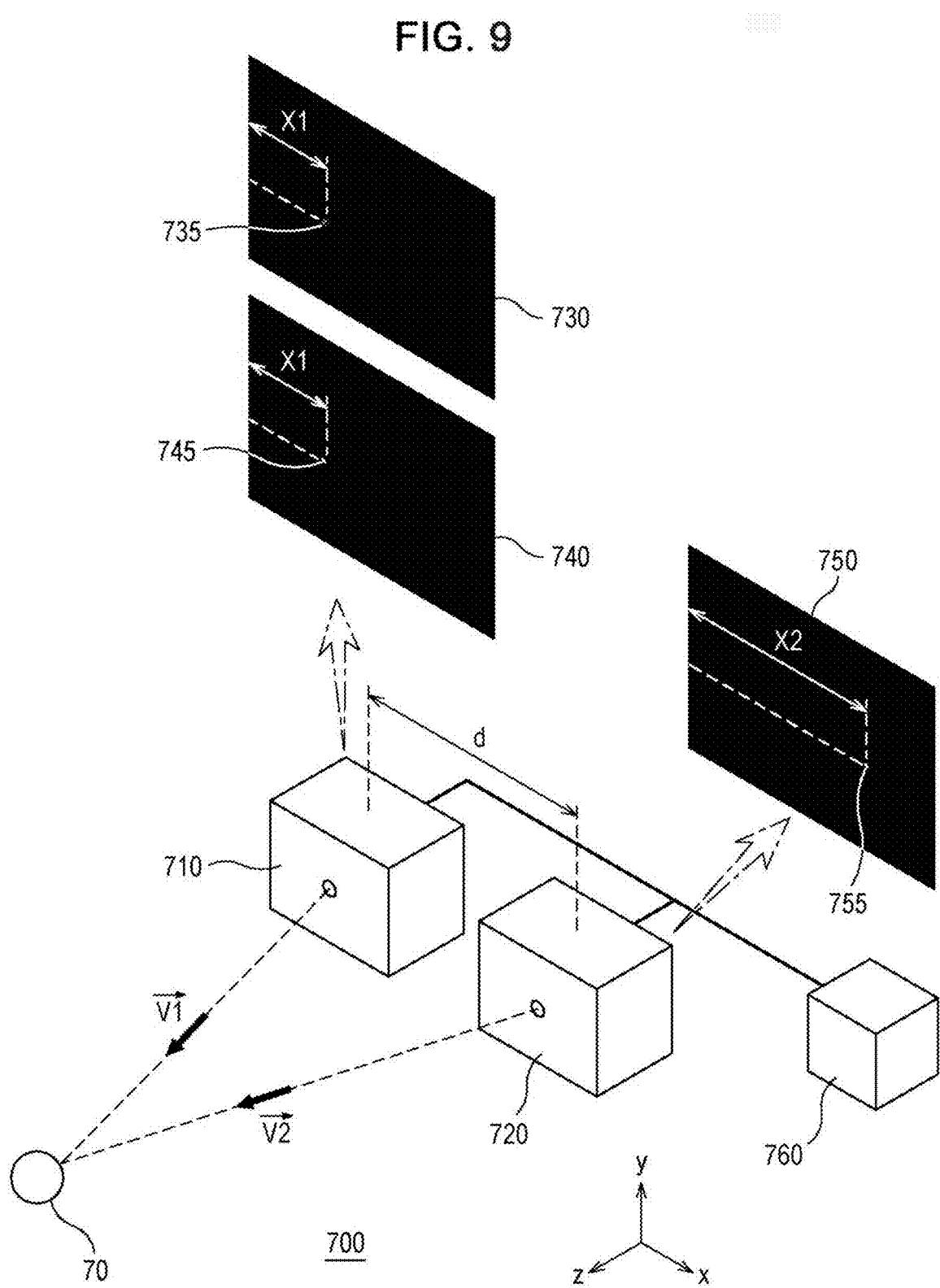
FIG. 9 is a view illustrating a method of determining a posture and a location of a marker based on an image captured in an image capturing part of an optical tracking system according to an embodiment of the present disclosure.

In one embodiment, the light field image 600 may be outputted as a photo aggregate file including a plurality of unit images in which the depths of field are formed in regions C1, C2, C3 and C4 at different positions in the image sensor. The plurality of regions C1, C2, C3 and C4 may be at different positions in the unit images. At least two regions may be at the same position depending on the situation. As shown in FIG. 9, the photo aggregate file may be an aggregate format obtained by simply collecting a plurality of unit images physically separated from each other. Alternatively, the photo aggregate file may be a format in which a plurality of unit images is integrally combined with each other in a new extension manner. In one embodiment, each unit image may include color information and direction information of the light so as to have different depths of field. The direction of an arrow shown in FIG. 9 may indicate a direction in which the distance at which the depth of field is formed increases.

According to one embodiment, the processor may classify a plurality of unit images included in the light field image 600 according to the depth of field (DOF) at which an image is formed, and may output a unit image having a depth of field closer than a reference image (REF) or a depth of field farther than the reference image in response to the user's input. For example, the depth of field of the reference image may correspond to the depth of field of the region including the location of the marker.

In one embodiment, the light field image captured in the image capturing device may include N unit images that can be classified according to the depth of field. In one embodiment, the processor may classify N images according to the depth of field at which each of the N images is formed, and may select one of the N images in response to the user's input. In addition, the processor may output an image having a depth of field formed at an infinite focal length among the N images in order to obtain a clear pattern image from the light field image.

FIG. 9 is a view illustrating a method of determining a posture and a location of a marker based on images 730, 740 and 750 captured in image capturing parts 710 and 720 of an optical tracking system according to an embodiment of the present disclosure.

In one embodiment, a marker 70 may be positioned within a field of view of first and second image capturing parts 710 and 720. In addition, the first image capturing part 710 may have a structure of a light field camera, and the second image capturing part 720 may have a structure of a camera for capturing an outgoing light image at a short focal length. The first image capturing part 710 may capture a first image 730 obtained by extracting an image from the light field image at an infinite focal length and including a pattern image 735, and a second image 730 obtained by extracting an image from the light field image at a short focal length. In addition, the second image capturing part 720 may capture a third image 750 including an outgoing light image directed to the second image capturing part 720 at a short focal length.

The depth of field of the first image 730 may be formed in a predetermined finite range around the position corresponding to an infinite focal length. The depths of field of the second and third images 740 and 750 may be formed in a predetermined finite range around the position corresponding to a short focal length. That is, the depths of field of the second and third images 740 and 750 may be formed in a predetermined finite range around the location of the marker 70.

In one embodiment, the first image capturing part 710 may extract the first image 730 captured at an infinite focal length and the second image 740 captured at a short focal length from the light field image captured by the first image capturing part 710 and may transmit them to a processor 760. The posture tracking part of the processor 760 may track the posture of the marker based on the size of at least a portion (or region) of the pattern included in the pattern image 735 of the first image 730 and the reference coordinates of an aperture region 745.

In one embodiment, the posture tracking part of the processor 760 may determine the posture of the marker based on the first image 730 obtained by extracting an image from the light field image at an infinite focal length in which a part of the pattern surface visible through the aperture is captured by the first image capturing part 710. The posture tracking part may also determine the location of each sub-pattern forming a pattern in the entire pattern based on the pattern image 735 included in the first image 730 and may determine the posture of the marker based on the result.

The pattern image 735 is identifiably captured in the first image 730, and the location of the aperture region 745 may be identifiably captured in the second image 740. In one embodiment, the first image capturing part 710 and the second image capturing part 720 may be disposed at the same height (e.g., the same height in the Y axis direction) from the ground. Thus, the aperture region 745 captured in the second image 740 and the aperture region 755 captured in the third image 750 may have the same height in the second and third images 740 and 750, respectively.

In one embodiment, the location tracking part of the processor 760 may determine the location of the marker in a three-dimensional space based on the disparity between the reference coordinates of the outgoing light image captured in the second and third images 740 and 750. The distance X1 at which the aperture region 745 is positioned in the second image 740 in a direction parallel to the ground surface (e.g., the X axis direction) may differ from the distance X2 at which the aperture region 755 is positioned in the third image 750 in a direction parallel to the ground surface. For example, the distance X2 may be larger than the distance X1. In addition, the first and second image capturing parts 710 and 720 may be spaced apart by a predetermined distance d. The location tracking part of the processor 760 may use the information on the predetermined distance d in the course of determining the location of the marker using triangulation.

On the other hand, the size of the region formed by the pattern image 735 in the first image 730 may be changed depending on at least one of the distance from the capturing position of the pattern image 735 (for example, the position of the image capturing part) to the marker and the location of the marker.

Figure 10:
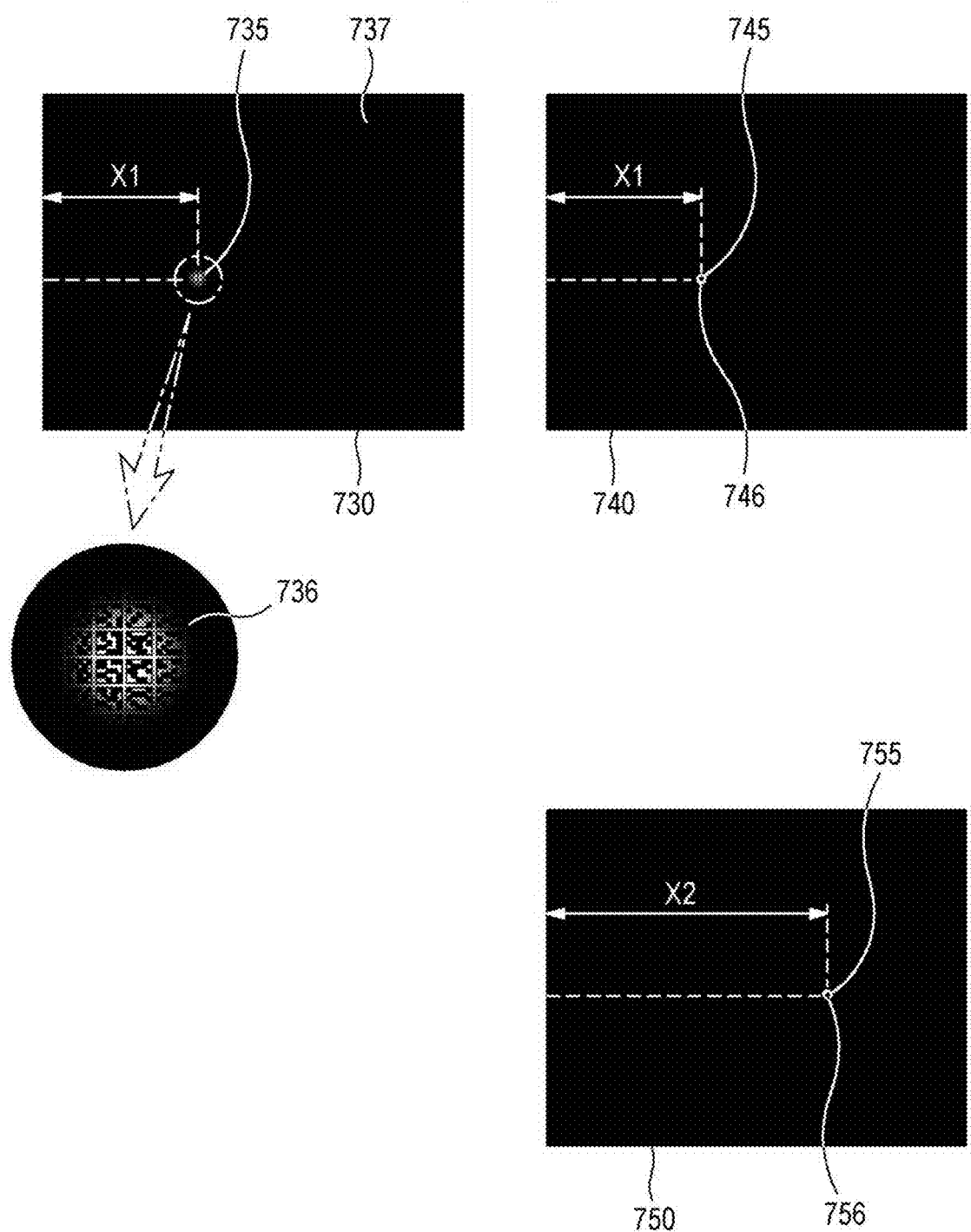
FIG. 10 is a view showing an image captured by the optical tracking system shown in FIG. 9.

According to one embodiment, the location tracking part of the processor 760 may extract reference coordinates of the aperture regions 745 and 755 on the captured second and third images 740 and 750 and may determine the location of the marker based on these reference coordinates. For example, if the aperture of the marker has a circular shape, the pattern image 735 and the aperture region 745 may appear as a substantially circular shape as shown in FIG. 10.

In one embodiment, the location tracking part of processor 760 may determine the location of the marker using triangulation. Specifically, the location tracking part of processor 760 may determine the location of the marker based on the second image 740 obtained by extracting an image from the light field image, captured by the first image capturing part 710, at a short focal length and the third image 750 obtained by capturing the outgoing light emitted through the aperture in a direction different from an emission direction of the outgoing light directed to the first image capturing part 710 at a short focal length using the second image capturing part 720.

The location tracking part of the processor 760 may extract the reference coordinates of the aperture regions 745 and 755 from the second and third images 740 and 750 captured by the first and second image capturing parts 710 and 720 and then may calculate the location of the marker using triangulation based on the reference coordinates. More specifically, the location tracking part may calculate the location of the marker using the reference coordinates of the aperture regions 745 and 755 and the geometrical relationship between the directions $\vec{V1}$ and $\vec{V2}$ in which the first and second image capturing parts 710 and 720 look at the marker.

According to one embodiment, the posture tracking part may determine the location of each sub-pattern from the pattern image 735. In order to extract information for the tracking of the marker from the pattern image, the processor 760 may first read sub-patterns from the pattern image 735. Then, the processor 760 may calculate the location (coordinates) of each of the read sub-patterns in the entire pattern.

FIG. 10 is a view showing an image captured by the optical tracking system shown in FIG. 9.

In the optical tracking system shown in FIG. 9, the first image capturing part 710 may acquire a light field image. The light field image may include a plurality of unit images having different depths of field. The first image capturing part 710 may extract a first image 730 captured at an infinite focal length and a second image 740 captured at a short focal length from the light field image. The size of the region of the pattern image 735 in the first image 730 captured at an infinite focal length may be larger than the size of the aperture region 745 in the second image 740 captured at a short focal length.

In the first image 730, the boundary portion 736 surrounding the pattern image 735 may correspond to the position of the aperture of the marker 70. When the outgoing light passes through the aperture, the outgoing light emitted through the edge of the aperture of the marker 70 may be captured by a camera in a blurred form due to diffraction, internal reflection, aperture vignetting, focal depth or the like. Since the boundary portion 736 is formed in a blurred state, the boundary portion 736 may not be distinguished from the peripheral portion 737. Further, the peripheral portion 737 is a portion that is relatively darker than the pattern surface 735 and may be corrected in an imageless form (for example, a black-out state) in an image processing process. Therefore, when the location tracking part of the processor 760 measures the reference coordinates of the pattern image 735, an error may occur due to the phenomenon that the boundary portion 736 is captured in a blurred state. Thus, the location tracking part may track the location of the marker based on the reference coordinates of the aperture regions 745 and 755 clearly captured in the second and third images 740 and 750.

In one embodiment, the posture tracking part may determine the posture of the marker by reading the captured pattern image 735 in the first image 730. Furthermore, the location tracking part may determine the reference coordinates 746 of the captured aperture region 745 in the second image 740 and the reference coordinates 756 of the captured aperture region 755 in the third image 750 and may determine the location of the marker based on the two reference coordinates 746 and 756.

Each of the pattern image 735 and aperture region 745 may be captured at a distance X1 from the left end of the first and second images 730 and 740. Alternatively, the aperture region 755 may be captured at a distance X2 from the left end in the third image 750. Therefore, the difference between the distance X1 and the distance X2 may be used to determine the location of the marker.

FIG. 11 is a block diagram of an optical tracking system 2 according to another embodiment of the present disclosure. Descriptions of the contents overlapping with those described in the above embodiment will be omitted.

The optical tracking system 2 according to another embodiment may include a marker 80, an image capturing device 800, and a processor 830. The image capturing device may include a first image capturing part 810 and a second image capturing part 820. In addition, each of the first and second image capturing parts 810 and 820 may have a structure of a light field camera. The processor 830 may receive a light field image in which different portions of a pattern are captured, from each of the first and second image capturing parts 810 and 820 and may track the location and the posture of the marker 10 based on the light field image.

In one embodiment, the first image capturing part 810 may include a lens 811, a lens array 812 and an image sensor 813. The second image capturing part 820 may include a lens 821, a lens array 822 and an image sensor 823. Accordingly, each of the first and second image capturing parts 810 and 820 may generate one light field image at one shot. In addition, the first and second image capturing parts 810 and 820 may constitute a stereoscopic part and may have a configuration of a coaxial illumination camera.

In one embodiment, each of the first and second image capturing parts 810 and 820 may include at least one light source 816 or 826 that irradiates light toward the marker 80 or the pattern surface 85 in order to enhance the light incident on the image capturing device 800 through the optical system 82 so that the pattern can be well identified outside the marker 80. Each of the first and second image capturing parts 810 and 820 may include a beam splitter 815 or 825 that irradiates the light generated from the light source 816 or 826 toward the marker 80 through the lens 811 or 821.

In one embodiment, the processor 830 may include a posture tracking part 832 for determining the posture of the marker 80 based on a first image obtained by capturing a part of the pattern surface 85 viewed through the aperture 83 at an infinite focal length, a location tracking part 831 for determining the location of the marker 80 based on second and third images respectively obtained by capturing the outgoing lights emitted through the aperture 83 in different directions at a focal length shorter than the infinite focal length, and an ID distinguishing part 833 for distinguishing the markers attached to the respective targets through the IDs of the markers to track the locations and the postures of the markers. The ID distinguishing part 833 may distinguish the ID of the marker 80 from the pattern image included in the first image.

Figure 12:
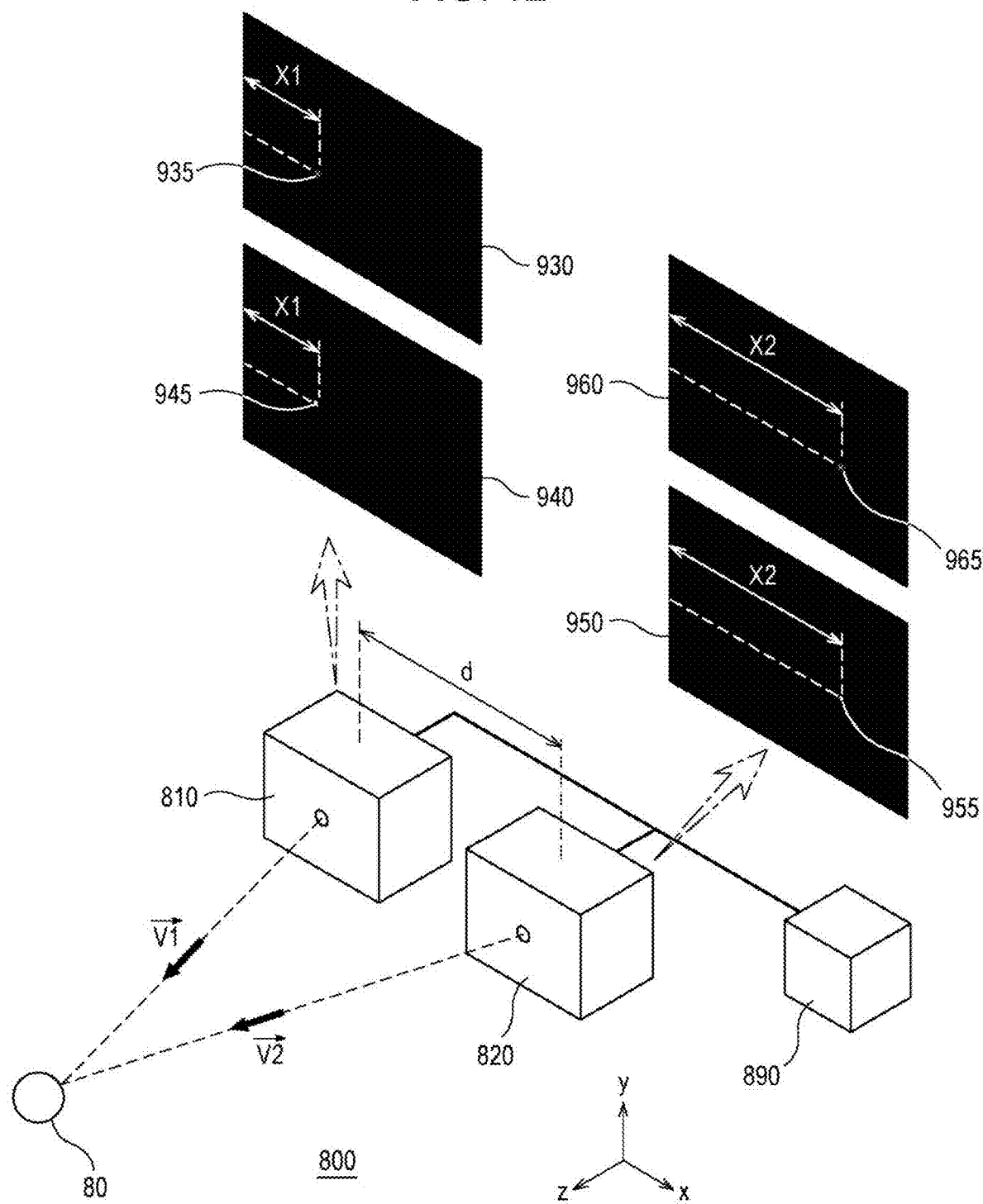
FIG. 12 is a view for illustrating a method of determining a posture and a location of a marker based on an image captured in an image capturing part of the optical tracking system according to another embodiment of the present disclosure.
Figure 13:
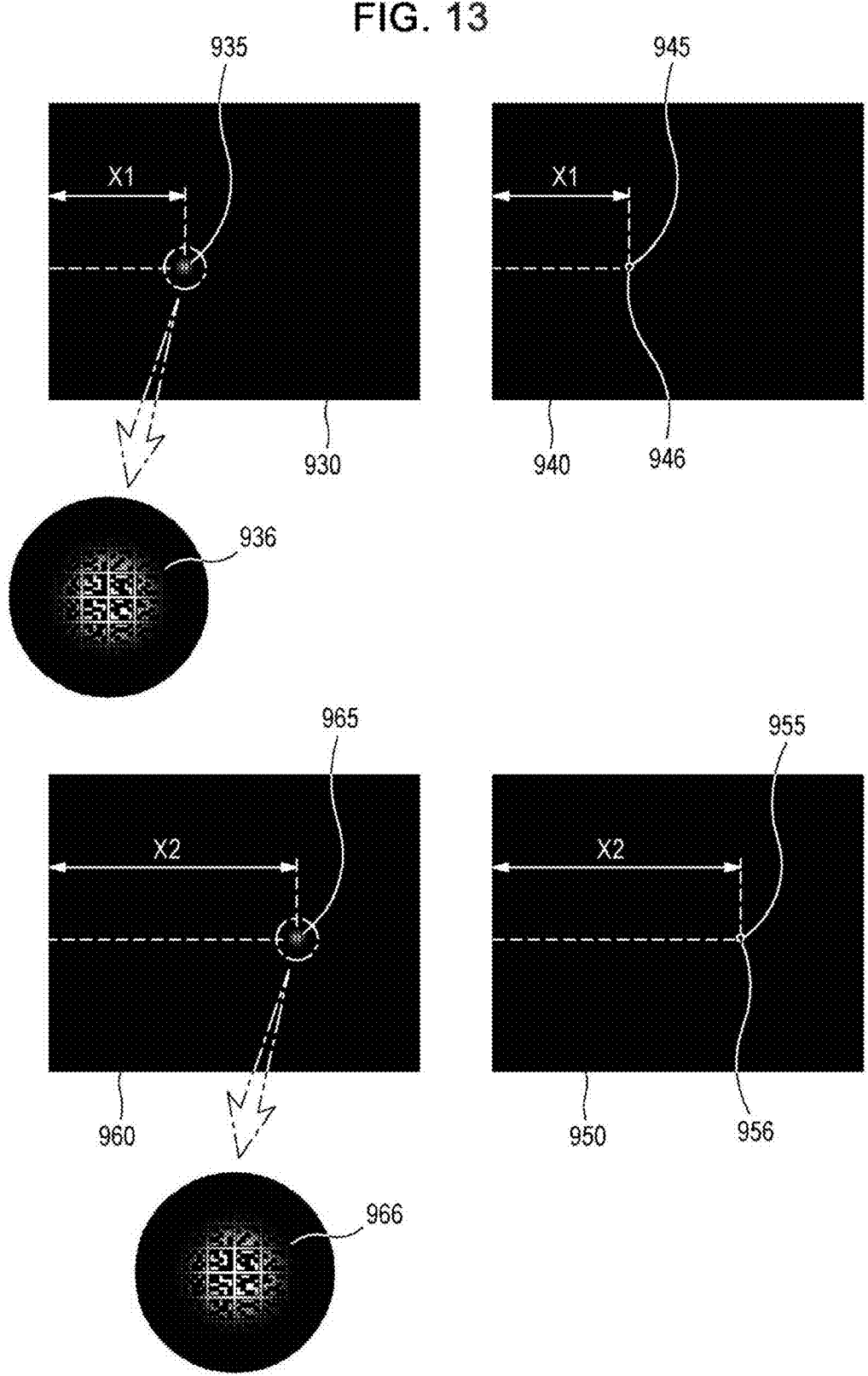
FIG. 13 is a view illustrating an image captured by the optical tracking system according to another embodiment of the present disclosure.

FIG. 12 is a view for illustrating a method of determining the posture and the location of the marker based on the image captured in the image capturing part of the optical tracking system 2 according to another embodiment of the present disclosure. FIG. 13 is a view illustrating the image captured by the optical tracking system 2 according to another embodiment of the present disclosure.

Referring to FIG. 3, the first image capturing part 810 of the optical tracking system 2 may generate a first light field image including a first portion of a pattern and the second image capturing part 820 may generate a second light field image including a second portion of a pattern differing from the first portion. Each of the first and second light field images may include a plurality of unit images having different depths of field.

In one embodiment, the posture tracking part of the processor 830 may determine the posture of the marker based on a first image 930 obtained by extracting an image from the light field image at an infinite focal length in which a part of the pattern surface viewed through the aperture is captured by the first image capturing part 810. The location tracking part of the processor 830 may determine the location of the marker based on a second image 940 obtained by extracting an image from the light field image, generated by the first image capturing part 810, at a short focal length and a third image 950 obtained by extracting an image from the light field image, generated by the second image capturing part 820, at a short focal length. Accordingly, the processor 830 may simultaneously track the location and the posture of the marker 80 without time difference and in real time.

According to one embodiment, the first image 930 is an image obtained by extracting an image from the light field image, generated by the first image capturing part 810, at an infinite focal length and may include a pattern image 935 in which a part of the pattern surface is identifiably captured. The second image 940 is an image obtained by extracting an image from the light field image, generated by the first image capturing part 810, at a short focal length including a region with the location of the maker 80 and may include an outgoing light image (e.g., an aperture region 945) in which the outgoing light directed to the first image capturing part 810 is captured. The third image 950 is an image obtained by extracting an image from the light field image, generated by the second image capturing part 820, at a short focal length including a region with the location of the maker 80 and may include an outgoing light image (e.g., an aperture region 955) in which the outgoing light directed to the second image capturing part 820 is captured.

In one embodiment, the posture tracking part of the processor may track the posture of the marker 80 based on a fourth image 960 extracted from a second light field image captured in the second image capturing part 820. Specifically, the second image capturing part 820 may transmit to the processor 830 the fourth image 960 including the pattern image 965 in which a part of the pattern surface is identifiably captured, as an image extracted an image captured at an infinite focal length from the second light field image generated by the second image capturing part 820. The location tracking part of the processor 830 may determine the location of the pattern image 965 captured in the fourth image 960 in the entire region of the pattern surface of the marker and may determine the posture of a target based on the location thus determined.

In the first image 930, the boundary portion 936 surrounding the pattern image 935 may correspond to the position of the aperture of the marker 80. In the fourth image 960, the boundary portion 966 surrounding the pattern image 965 may correspond to the position of the aperture of the marker 80. Since these boundary portions 936 and 966 may be captured in a blurred state, the posture of the marker may be determined based on the first and third images 940 and 950 in which the aperture regions 945 and 955 are clearly captured.

In one embodiment, the location tracking part of the processor 830 may determine the posture of the target based on an average value of the posture of the target determined from the first image 930 and the posture of the target determined from the fourth image 960. This makes it possible to improve the accuracy of the location of the tracked marker 80.

In one embodiment, the location tracking part of the processor 830 may determine the location of the marker based on the second and third images 940 and 950. That is, the processor may determine the reference coordinates 946 of the border surrounding the aperture region 945 captured in the second image 940 and the reference coordinates 956 of the border surrounding the aperture region 955 captured in the third image 950, and may determine the posture of the marker based on the two reference coordinates 946 and 956.

In the first and second images 930 and 940, the pattern image 935 and the aperture region 945 may be captured at a distance X1 from the left end. In the third and fourth images 950 and 960, the aperture region 955 and the pattern image 965 may be captured at a distance X2 from the left end. Accordingly, the location tracking part of the processor 830 may determine the location of the marker on a three-dimensional space based on the difference between the distance X1 and the distance X2. In addition, the location tracking part may construct a stereoscopic image based on the second and third images 940 and 950 and may determine the location of the marker 80 on the three-dimensional space.

<Marker Tracking Method>

FIG. 14 is a flowchart showing an optical tracking method (S1200) according to another embodiment of the present disclosure. Hereinafter, the respective steps of a marker tracking method will be described in more detail with reference to the drawings. Descriptions of the contents overlapping with those described in the above embodiment will be omitted.

Referring first to FIG. 2, in step S1210, a first image obtained by extracting an image from the light field image, captured by the first image capturing part 110, at an infinite focal length and including a pattern image in which a part of the pattern surface 15 is identifiably captured, a second image obtained by extracting an image from the light field image at a short focal length and obtained by capturing the outgoing light emitted through the aperture 13 in a first direction, and a third image obtained by capturing the outgoing light emitted through the aperture 13 in a second direction different from the first direction using the second image capturing part 120, may be captured. Next, in step S1220, the posture of the marker may be determined based on the first image. Then, in step S1230, the location of the marker may be determined based on the second image and the third image.

Figure 15:
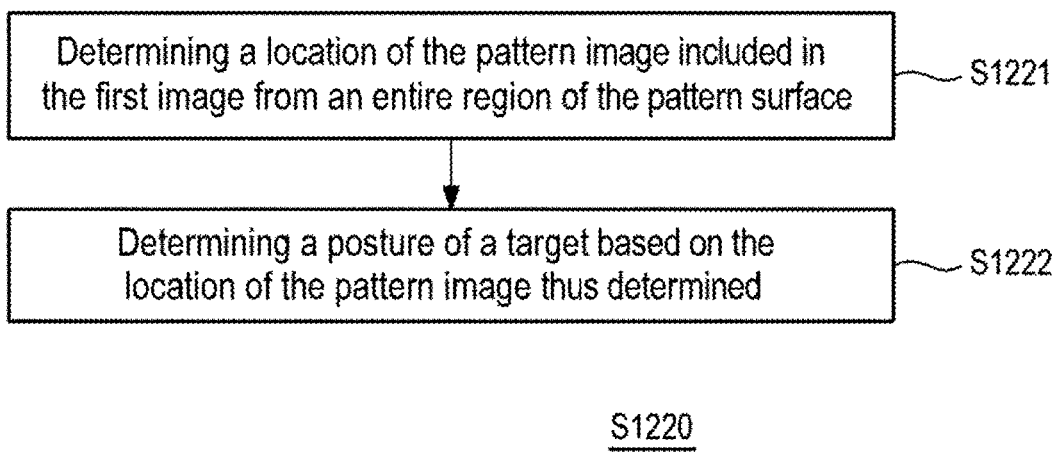
FIG. 15 is a flowchart showing a step of determining a posture of a marker in the optical tracking method shown in FIG. 14.

FIG. 15 is a flowchart showing the step S1220 of determining the posture of the marker in the optical tracking method (S1200) shown in FIG. 14.

Referring to FIG. 5, the step S1220 of determining the posture of the marker may include a step S1221 of determining the location of the pattern image 735 included in the first image 730 in the entire region of the pattern surface and a step S1222 of determining the posture of the target based on the location of the pattern image 735 thus determined.

In the step S1221, the processor may extract at least one sub-pattern from the pattern image. For example, referring to FIG. 4, the processor may extract at least one sub-pattern 350 through the pattern window 340 of a predetermined size from the pattern image obtained by the image capturing device, When at least one sub-pattern is extracted in this manner, in the step S1222, the processor may determine the posture of the marker based on the at least one sub-pattern thus extracted. Specifically, the processor may determine the location of the sub-pattern in the pattern, and then the processor may determine the posture of the marker based on the determined location of the sub-pattern in the pattern. That is, the processor may determine the posture of the marker based on the determined location of the sub-pattern in the entire pattern.

Figure 16:
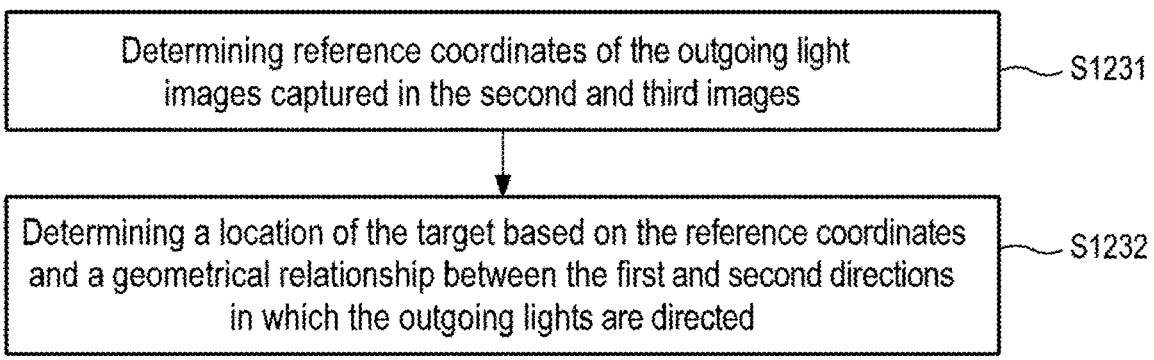
FIG. 16 is a flowchart showing a step of determining a location of a marker in the optical tracking method shown in FIG. 15.

FIG. 16 is a flowchart showing a step S1230 of determining the location of the marker in the optical tracking method (S1200) shown in FIG. 15.

Referring to FIG. 5, the step S1230 of determining the location of the marker may include a step S1231 of determining the reference coordinates of the aperture regions 745 and 755 including the outgoing light images captured in the second and third images 740 and 750 and a step S1232 of determining the location of the target based on the reference coordinates thus determined and the geometrical relationship between the directions in which the outgoing lights are directed.

The processor may determine the location of the marker 70 based on the triangulation using the reference coordinates of the respective outgoing light images 745 and 755 (e.g., the coordinates of the center of the aperture region) and the geometrical relationship between the directions $\overrightarrow{V1}$ and $\overrightarrow{V2}$ in which the first and second image capturing parts 710 and 720 look at the marker 70. In the above embodiments, the location of the marker is determined using the triangulation. However, the present disclosure is not limited thereto. Methods other than the triangulation may be used.

In the embodiment described with reference to FIG. 14, the processor determines the posture of the marker after determining the location of the marker. In another embodiment, the processor may determine the posture of the marker prior to determining the location of the marker. In some embodiments, the processor may determine the location and the posture of the marker by processing the same in parallel.

Although the method has been described through specific embodiments, the method may also be embodied as computer-readable codes in a computer-readable recording medium. The computer-readable recording medium includes all kinds of recording devices that store data that can be read by a computer system. Examples of the computer-readable recording medium may include a CD-ROM, a USB memory device and the like. In addition, the computer-readable recording medium may be distributed to computer systems that are connected through a network, and a computer-readable code may be stored and executed in a distributed manner. In addition, functional programs, codes, and code segments for implementing the embodiments above may be easily inferred by the programmers who are skilled in the art.

Although the present disclosure has been described in relation to some embodiments, it should be noted that there may be various modifications and changes without departing from the spirit and scope of the present disclosure, which can be understood by those skilled in the art. In addition, such modifications and changes should be construed to belong to the scope of the claims appended herein.

What is claimed is:

1. An optical tracking system for tracking a location and a posture of a marker which is attachable to a target and configured so that a pattern surface formed inside the marker is visible through an optical system formed in an aperture, comprising:
   an image capturing device including a first camera configured to capture at least a part of the marker to generate a light field image, which includes a plurality of unit images, and a second camera configured to capture a first outgoing light emitted from the aperture; and
   a processor configured to determine the posture of the marker based on a first image, which captures a part of the pattern surface and is obtained by extracting an image from the plurality of unit images of the light field image at an infinite focal length, and to determine the location of the marker based on a second image obtained by extracting an image from the plurality of unit images of the light field image at a short focal length shorter than the infinite focal length and a third image obtained by capturing, by the second camera, the first outgoing light emitted from the aperture in a direction different from an emission direction of a second outgoing light directed to the first camera,
   wherein the first camera comprises:
      a lens having one focal length;
      a lens array including a plurality of sub-lenses configured to disperse a light coming through the lens and condense the light at a plurality of points formed at different locations; and
      an image sensor configured to sense the light that has passed through the lens array and output the light field image, which includes the plurality of unit images corresponding to the plurality of points and having different depths of field, at one shot.

2. The optical tracking system of claim 1, wherein the processor includes:
   a posture tracker configured to determine the posture of the marker based on the first image in which the part of the pattern surface visible through the aperture is captured at the infinite focal length; and
   a location tracker configured to determine the location of the marker based on the second and third images in which the first and second outgoing lights emitted from the aperture in different directions are respectively captured.

3. The optical tracking system of claim 2, wherein the first image is obtained by extracting the image from the plurality of unit images of the light field image at the infinite focal length and includes a pattern image in which the part of the pattern surface is identifiably captured,
   the second image is obtained by extracting the image from the plurality of unit images of the light field image at a focal length of a predetermined range including a location of the target and includes a first outgoing light image in which the second outgoing light directed to the first camera is captured, and
   the third image includes a second outgoing light image in which the first outgoing light directed to the second camera is captured.

4. The optical tracking system of claim 3, wherein the posture tracker is configured to determine a location of the pattern image from an entire region of the pattern surface and to determine a posture of the target based on the location of the pattern image.

5. The optical tracking system of claim 3, wherein the location tracker is configured to determine reference coordinates of the first and second outgoing light images captured in the second and third images and to determine the location of the target based on the reference coordinates and a geometrical relationship between the marker and the first and second cameras.

6. The optical tracking system of claim 5, wherein the location tracker is configured to determine the location of the marker on a three-dimensional space based on a disparity between the reference coordinates of the first and second outgoing light images captured in the second and third images.

7. The optical tracking system of claim 3, wherein the location tracker is configured to construct a stereoscopic image based on the second and third images and to determine the location of the marker on a three-dimensional space.

8. An optical tracking system for tracking a location and a posture of a marker which is attachable to a target and configured so that a pattern surface formed inside the marker is visible through an optical system formed in an aperture, comprising:
   an image capturing device including a first camera and a second camera, each of the first and second cameras configured to capture at least a part of the marker to generate a light field image, which includes a plurality of unit images; and
   a processor configured to determine the posture of the marker based on a first image, which captures a first part of the pattern surface and is obtained by extracting an image from the plurality of unit images of the light field image, generated by the first camera, at an infinite focal length, and to determine the location of the marker based on a second image obtained by extracting an image from the plurality of unit images of the light field image, generated by the first camera, at a first short focal length shorter than the infinite focal length and a third image obtained by extracting an image from the plurality of unit images of the light field image, generated by the second camera, at a second short focal length shorter than the infinite focal length,
   wherein each of the first and second cameras comprises:
      a lens having one focal length;
      a lens array including a plurality of sub-lenses configured to disperse a light coming through the lens and condense the light at a plurality of points formed at different locations; and
      an image sensor configured to sense the light that has passed through the lens array and output the light field image, which includes the plurality of unit images corresponding to the plurality of points and having different depths of field, at one shot.

9. The optical tracking system of claim 8, wherein the first image is obtained by extracting the image from the light field image at the infinite focal length and includes a pattern image in which the first part of the pattern surface is identifiably captured, the second image is obtained by extracting the image from the plurality of unit images of the light field image, generated by the first camera, at a focal length of a predetermined range including a location of the target and includes a first outgoing light image in which a first outgoing light directed to the first camera is captured, and the third image is obtained by extracting an image from the plurality of unit images of the light field image, generated by the second camera, at the focal length of the predetermined range and includes a second outgoing light image in which a second outgoing light directed to the second camera is captured.

10. The optical tracking system of claim 9, wherein the processor is configured to determine a location of the pattern image from an entire region of the pattern surface and to determine a posture of the target based on the location of the pattern image, and the processor is configured to determine reference coordinates of the first and second outgoing light images captured in the second and third images, respectively, and to determine the location of the target based on the reference coordinates and a geometrical relationship between the marker and the first and second cameras.

11. The optical tracking system of claim 10, wherein the second camera is configured to transmit to the processor a fourth image obtained by extracting an image from the plurality of unit images of the light field image, generated by the second camera, at the infinite focal length and including a pattern image in which a second part of the pattern surface is identifiably captured, and the processor is configured to determine a location of the pattern image captured in the fourth image from the entire region of the pattern surface and to determine the posture of the target based on the location of the pattern image.

12. The optical tracking system of claim 8, wherein the processor is configured to determine a location and a posture of the target from a pattern image captured in the first image.

13. An optical tracking method for tracking a location and a posture of a marker which is attachable to a target and configured so that a pattern surface formed inside the marker is visible through an optical system formed in an aperture by using a first camera including: a lens having one focal length; a lens array including a plurality of sub-lenses; and an image sensor, the optical tracking method comprising:

capturing a first image obtained by extracting an image from a light field image, which includes a plurality of unit images corresponding to a plurality of points and having different depths of field, captured by the first camera at an infinite focal length and including a pattern image in which a part of the pattern surface is identifiably captured, a second image obtained by extracting an image from the plurality of unit images of the light field image at a short focal length shorter than the infinite focal length and obtained by capturing an outgoing light emitted through the aperture in a first direction, and a third image obtained by capturing an outgoing light emitted through the aperture in a second direction different from the first direction using a second camera;

determining the posture of the marker based on the first image; and determining the location of the marker based on the second image and the third image, wherein, in the act of capturing the first image, the second image and the third image, the plurality of sub-lenses disperse a light coming through the lens and condense the light at the plurality of points formed at different locations, and the image sensor senses the light that has passed through the lens array and outputs the light field image at one shot.

14. The optical tracking method of claim 13, wherein the determining the posture of the marker includes:

determining a location of the pattern image included in the first image from an entire region of the pattern surface; and determining a posture of the target based on the location of the pattern image.

15. The optical tracking method of claim 13, wherein the determining the location of the marker includes:

determining reference coordinates of outgoing light images captured in the second and third images; and determining a location of the target based on the reference coordinates and a geometrical relationship between the first and second directions in which the outgoing lights are directed.

* * * * *